US011129519B2

(12) United States Patent
Wei et al.

(10) Patent No.: US 11,129,519 B2
(45) Date of Patent: Sep. 28, 2021

(54) SINGLE-USE ENDOSCOPE WITH BUILT-IN OPTICAL FIBERS AND FIXTURES

(71) Applicant: OTU Medical Inc., Fremont, CA (US)

(72) Inventors: XiBo Wei, Hayward, CA (US); GePing Liu, San Jose, CA (US); XiYi Wei, NingBo (CN)

(73) Assignee: OTU Medical Inc.

( * ) Notice: Subject to any disclaimer, the term of this patent is extended or adjusted under 35 U.S.C. 154(b) by 348 days.

(21) Appl. No.: 15/884,344

(22) Filed: Jan. 30, 2018

(65) Prior Publication Data

US 2018/0153381 A1   Jun. 7, 2018

Related U.S. Application Data

(63) Continuation-in-part of application No. 15/823,582, filed on Nov. 28, 2017, now abandoned, and a
(Continued)

(30) Foreign Application Priority Data

Nov. 24, 2016 (CN) .......................... 201611041752.8
Nov. 24, 2016 (CN) .......................... 201611041782.9

(51) Int. Cl.
*A61B 1/00* (2006.01)
*A61B 1/313* (2006.01)
*A61N 5/06* (2006.01)

(52) U.S. Cl.
CPC ...... *A61B 1/00165* (2013.01); *A61B 1/00002* (2013.01); *A61B 1/00066* (2013.01);
(Continued)

(58) Field of Classification Search
CPC .............. A61B 1/00032; A61B 1/0008; A61B 1/00103; A61B 1/00105; A61B 1/0011;
(Continued)

(56) References Cited

U.S. PATENT DOCUMENTS 5,651,783 A * 7/1997 Reynard ................ A61B 1/042
606/17
6,011,891 A * 1/2000 Katzir ........................ G01J 5/02
374/E13.003
(Continued)

*Primary Examiner* — Timothy J Neal
*Assistant Examiner* — William B Chou
(74) *Attorney, Agent, or Firm* — 5Suns; Chein-Hwa Tsao; Yuanhui Huang

(57) ABSTRACT

This present invention proposes new methods of designing single-use endoscopes with built-in optical fibers and operating fixtures. As compared to conventional endoscopes, a separate lumen is reserved for integrating a laser fiber along the insertion tube of the proposed endoscope, and an optical fiber placement device (OFPD) is correspondingly added in the endoscope handle for controlling the movement of the laser fiber. By sliding the slider or dialing the wheel of OFPD, a surgeon can conveniently control movement of the laser fiber. By pressing a retractable control stick in the OFPD, the surgeon can either push the laser fiber out from the endoscope's distal-end or pull back the laser fiber, further unlocking or locking the power switch of the laser fiber to avoid mis-operations. All these above operations can be performed by the surgeon's one-hand, including the routine deflections and rotations of the endoscope. Four implementations of the OFPD are introduced in this invention. In addition, an ultra-small optical fiber based pressure sensor can be added at the distal end of the endoscope upon applications.

38 Claims, 29 Drawing Sheets

Present Invention

Related U.S. Application Data continuation-in-part of application No. 15/854,009, filed on Dec. 26, 2017, and a continuation-in-part of application No. 15/246,636, filed on Aug. 25, 2016, now Pat. No. 9,942,452, and a continuation-in-part of application No. 15/649,485, filed on Jul. 13, 2017, now abandoned.

(52) U.S. Cl.
CPC ...... *A61B 1/00087* (2013.01); *A61B 1/00103* (2013.01); *A61B 1/00117* (2013.01); *A61B 1/00133* (2013.01); *A61B 1/313* (2013.01); *A61N 5/0601* (2013.01)

(58) Field of Classification Search
CPC ..... A61B 1/0052; A61B 1/0057; A61B 1/015; A61B 1/018; A61B 1/051; A61B 1/0676; A61B 1/0684; A61B 1/07; A61B 1/128; A61L 29/126; H04N 5/2252; H04N 5/2256; H04N 5/2257; H04N 5/374
See application file for complete search history.

(56) References Cited

U.S. PATENT DOCUMENTS

| | | | |
|---|---|---|---|
| 10,531,787 B2* | 1/2020 | Dillon | A61B 1/0052 |
| 2008/0260342 A1* | 10/2008 | Kuroiwa | A61B 5/0066 |
| | | | 385/133 |
| 2017/0215696 A1* | 8/2017 | Harrah | A61B 18/24 |
| 2018/0153381 A1* | 6/2018 | Wei | A61B 1/00117 |
| 2018/0271545 A1* | 9/2018 | Preiss | A61B 17/22 |

\* cited by examiner

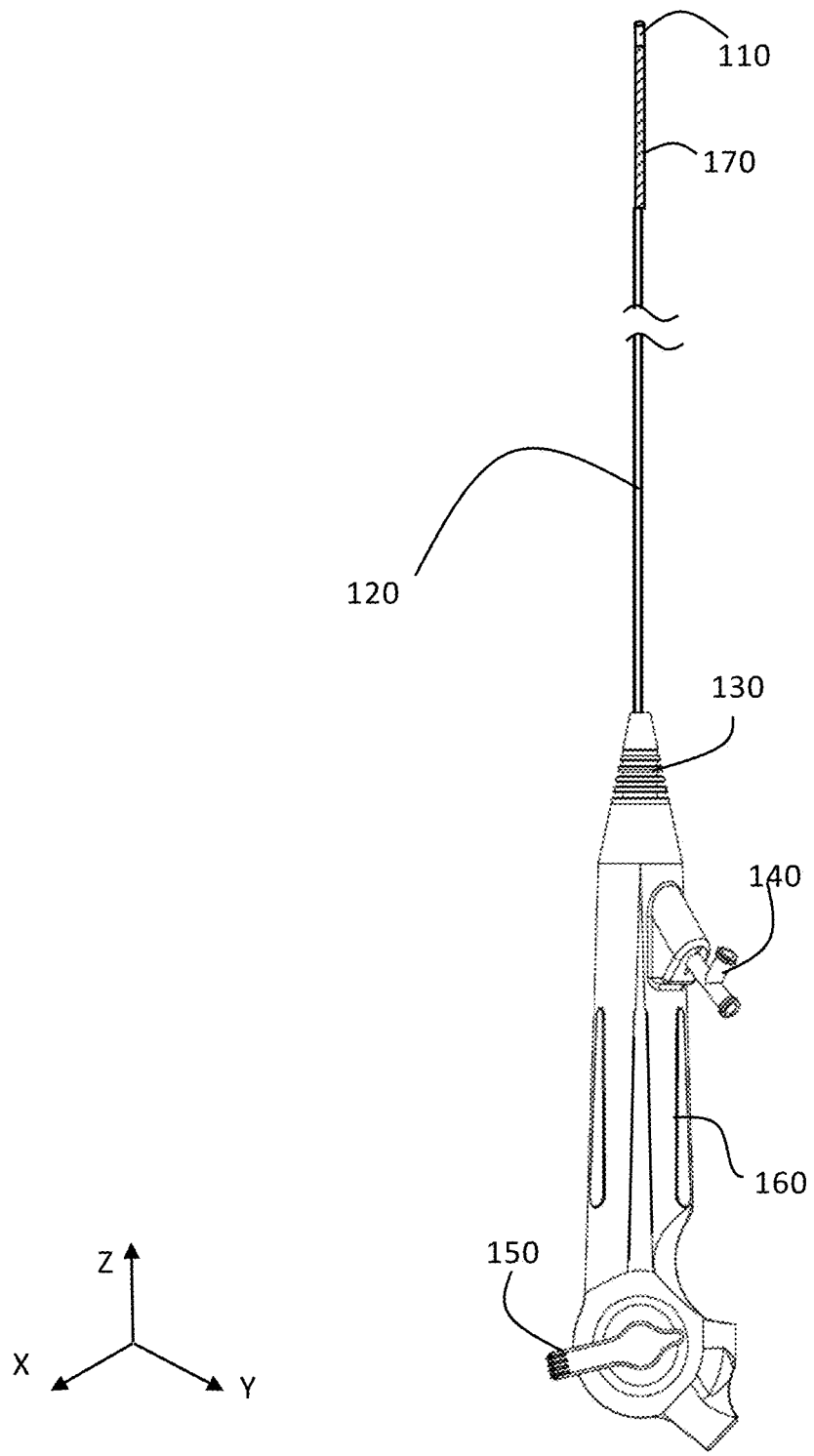
Figure 1. Present Invention

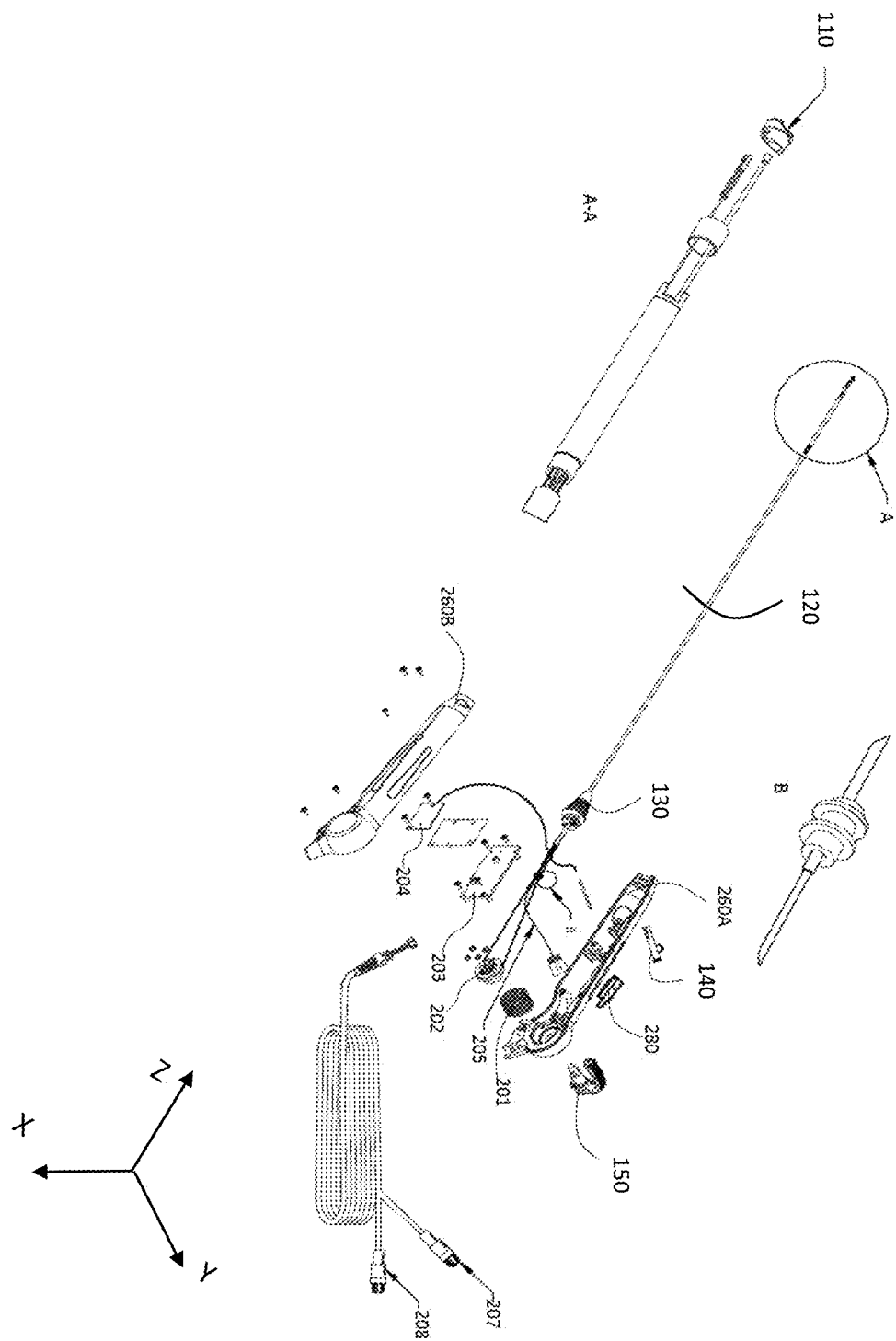
Figure 2. Present Invention

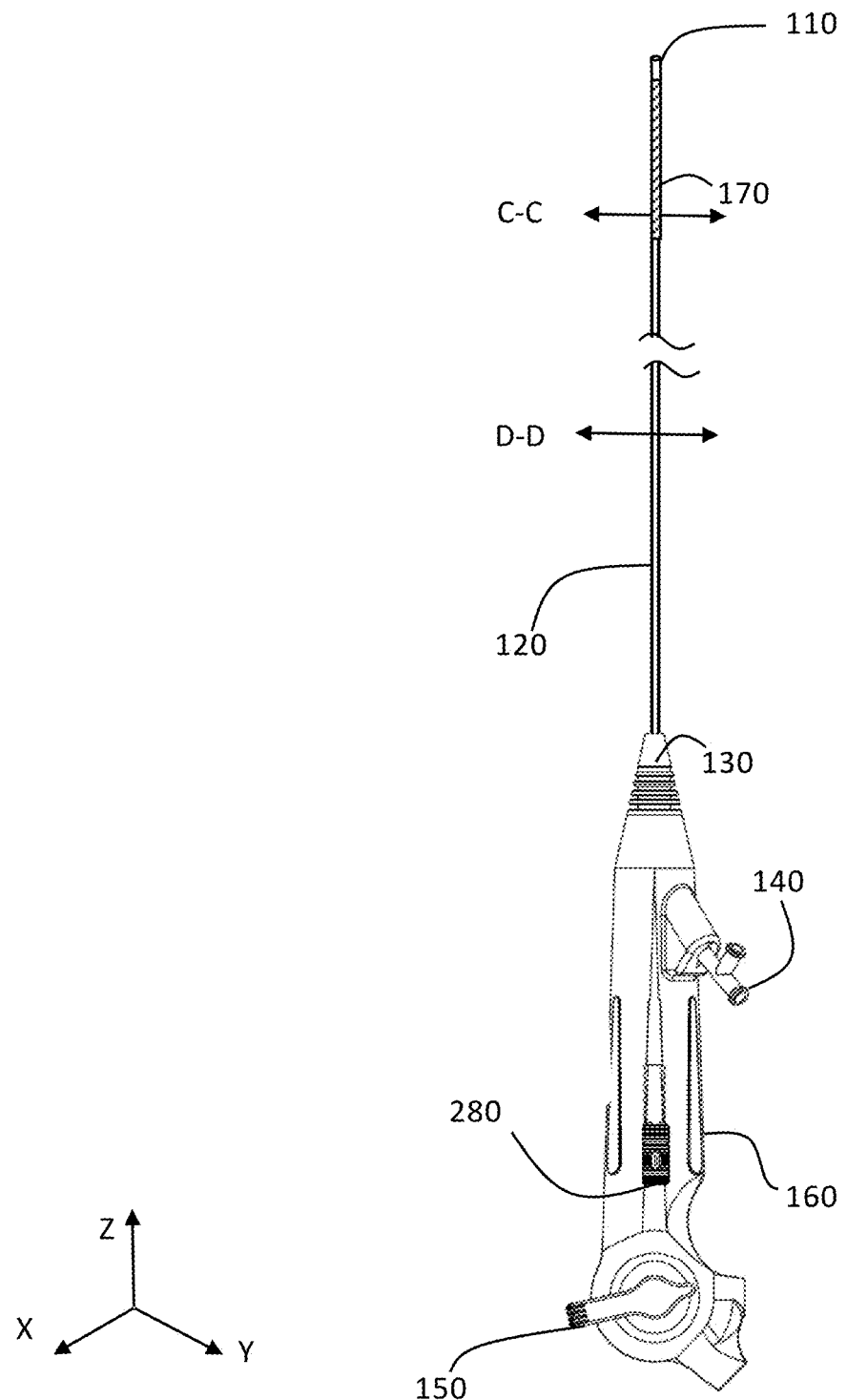
Figure 3. Present Invention

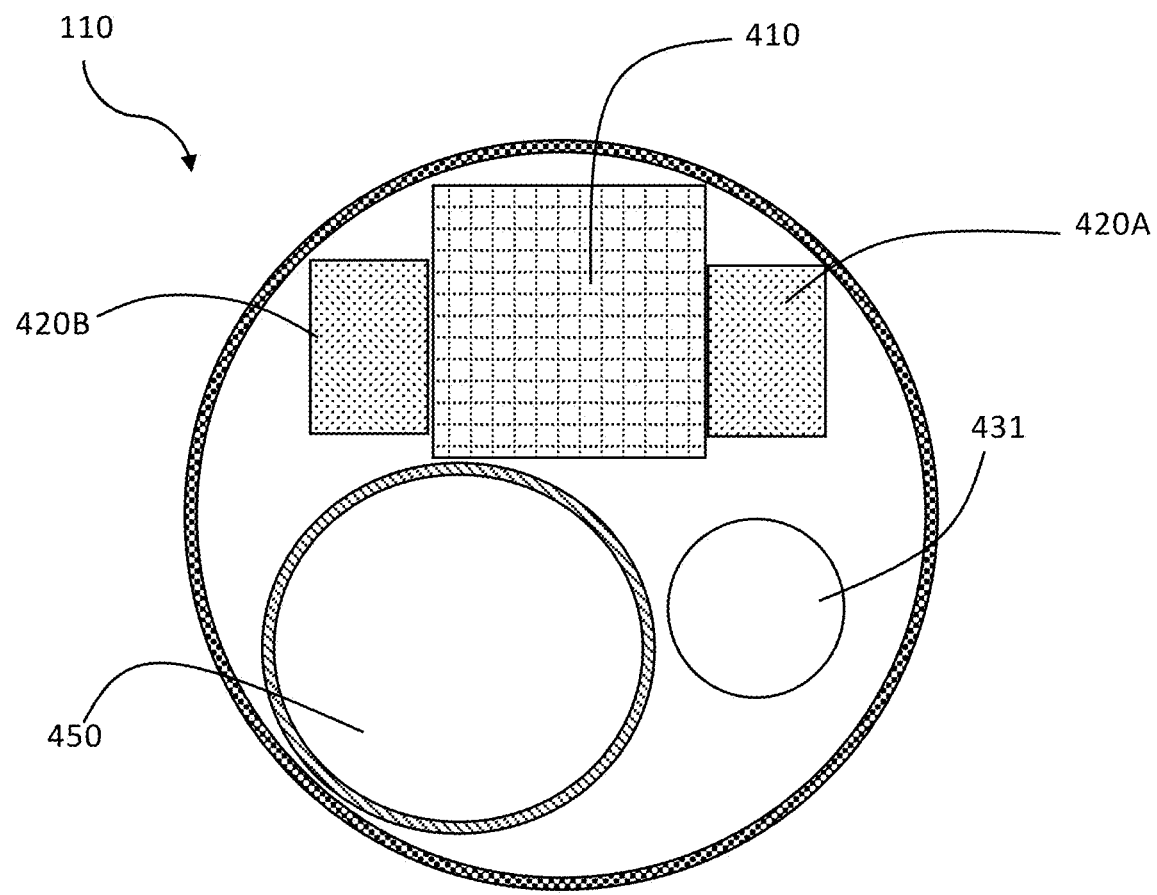
Figure 4. Present Invention

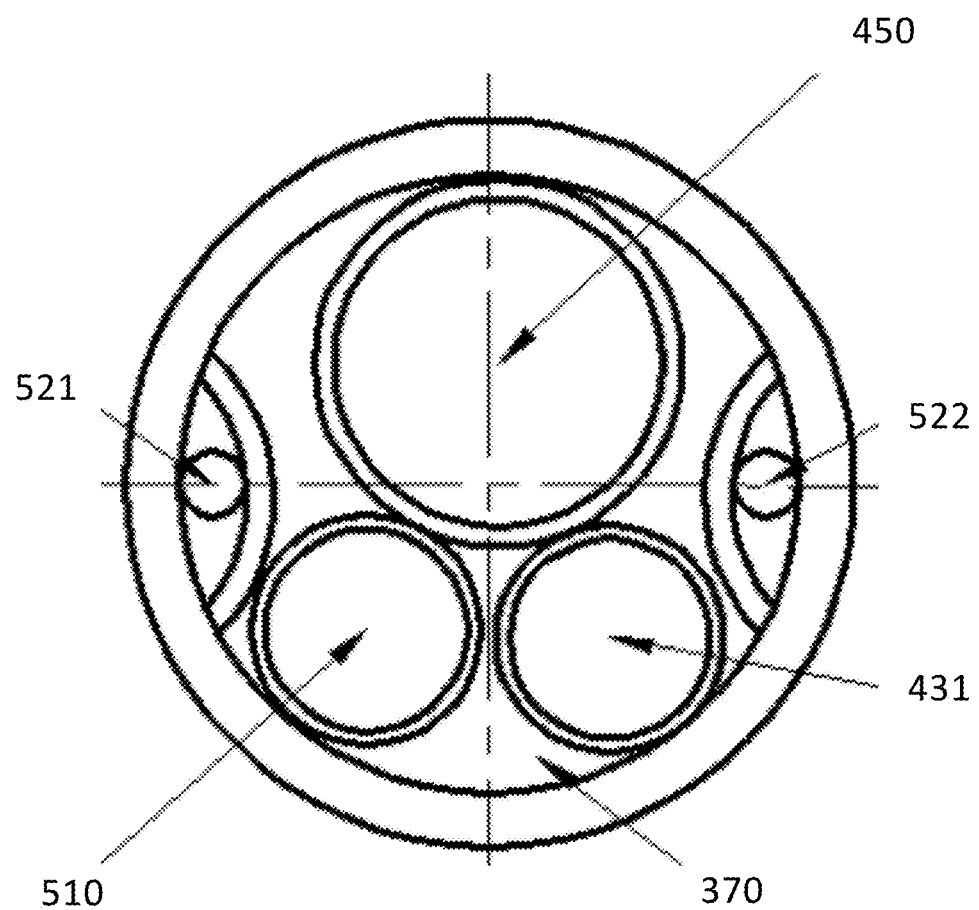
Figure 5. Present Invention

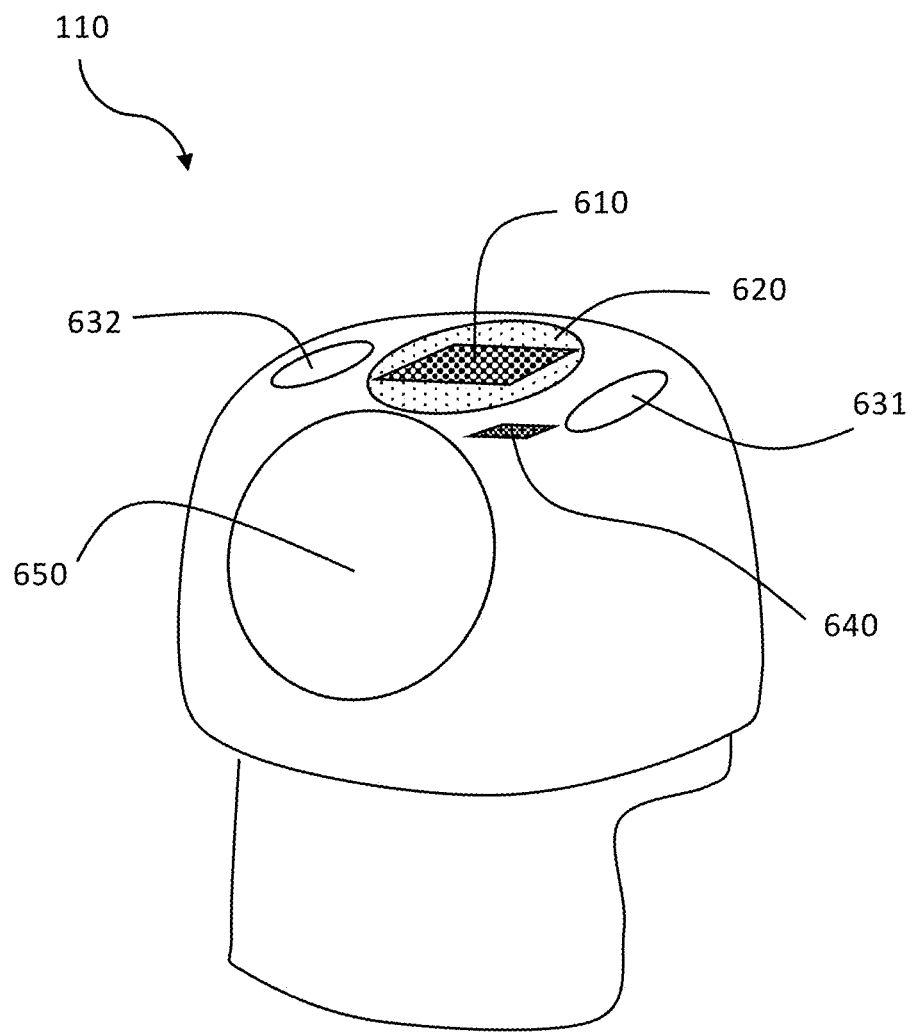
Figure 6. Present Invention

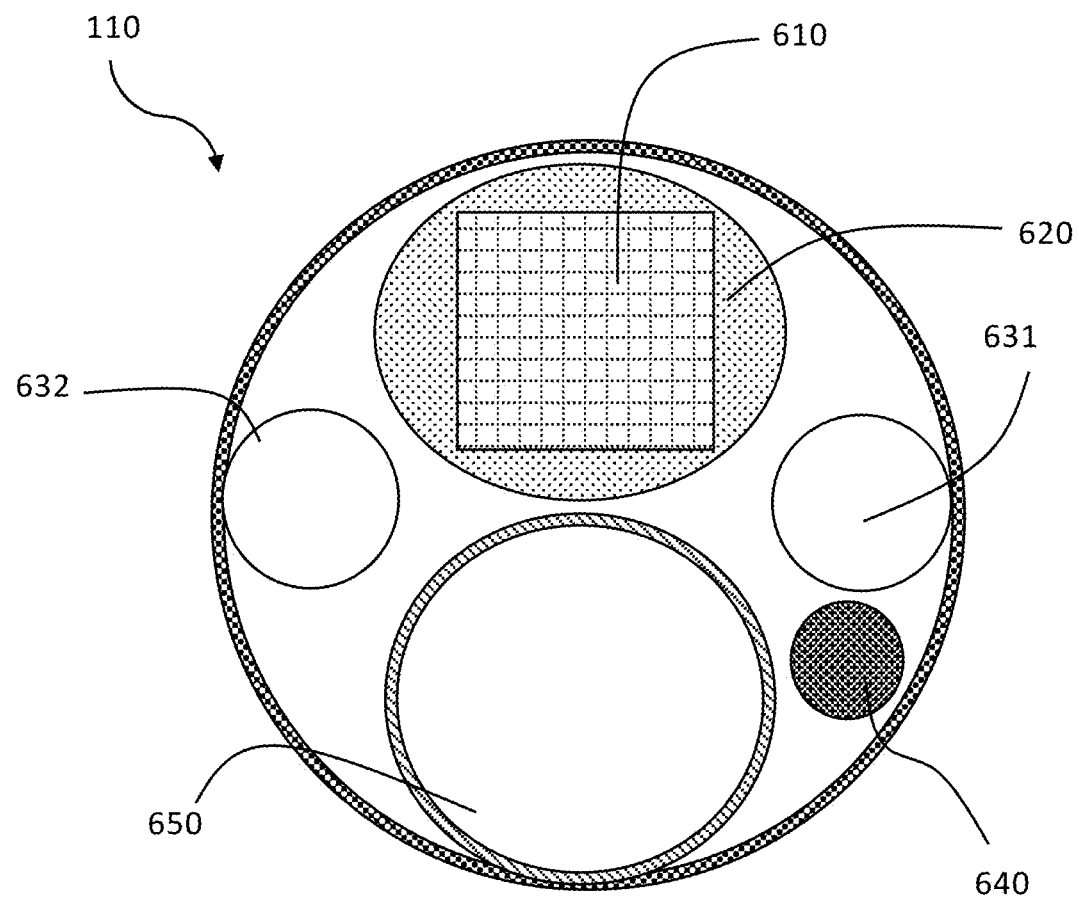
Figure 7. Present Invention

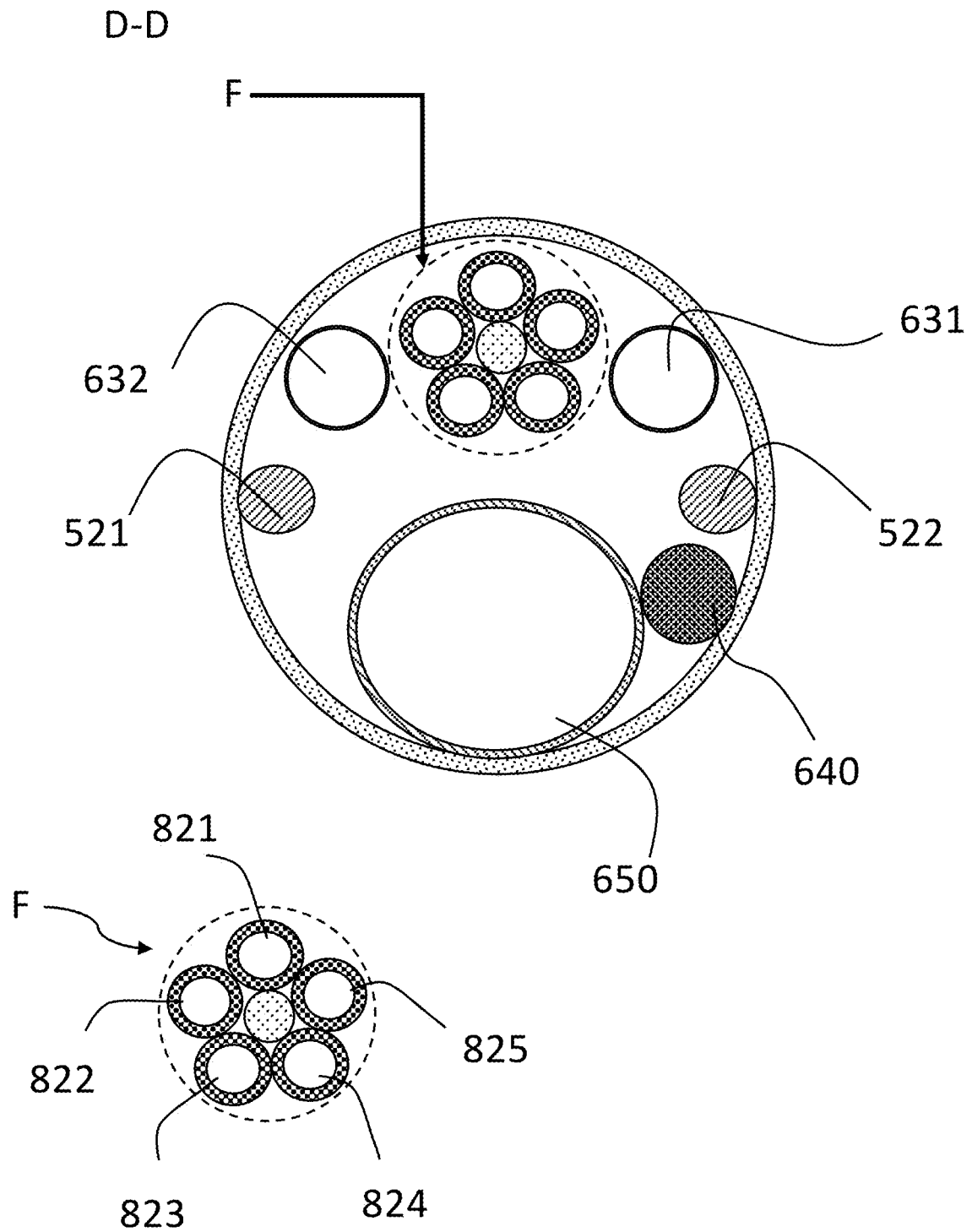
Figure 8. Present Invention

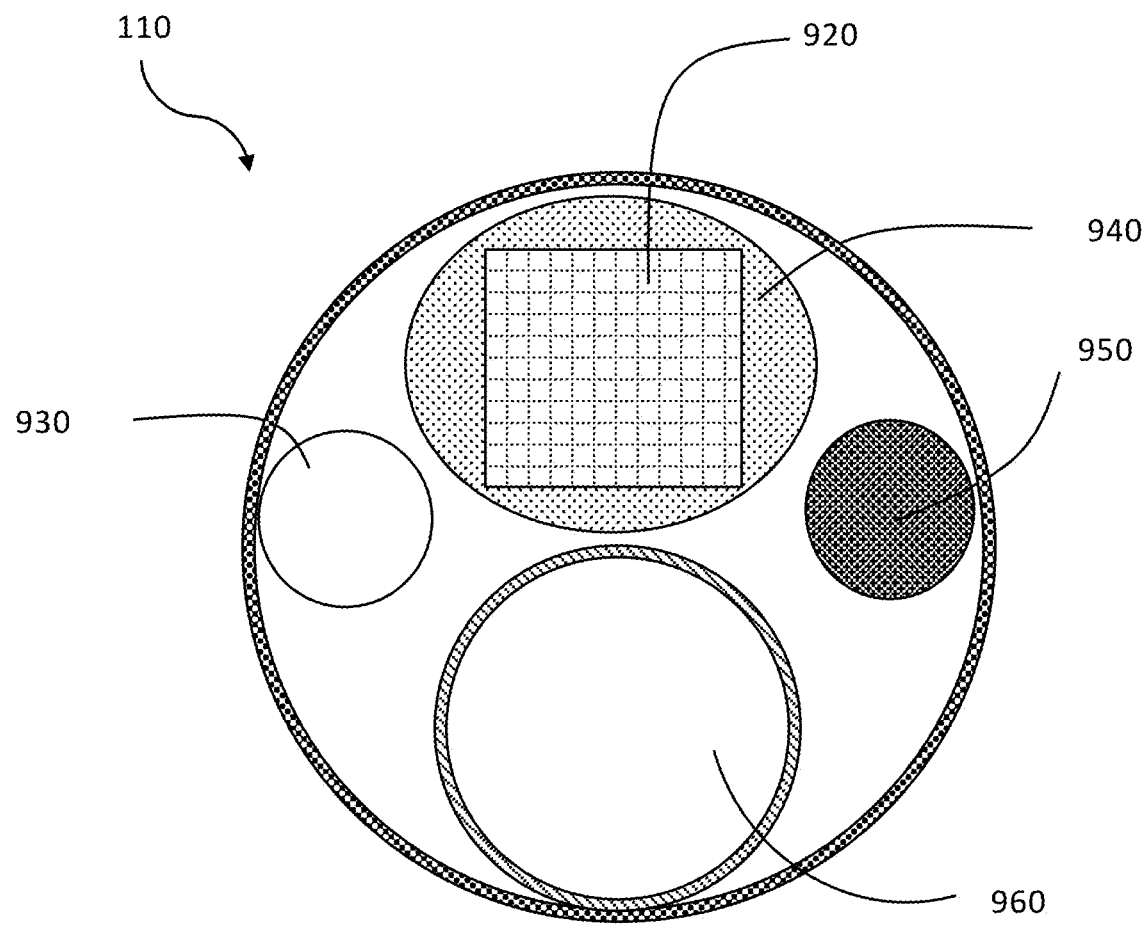
Figure 9. Present Invention

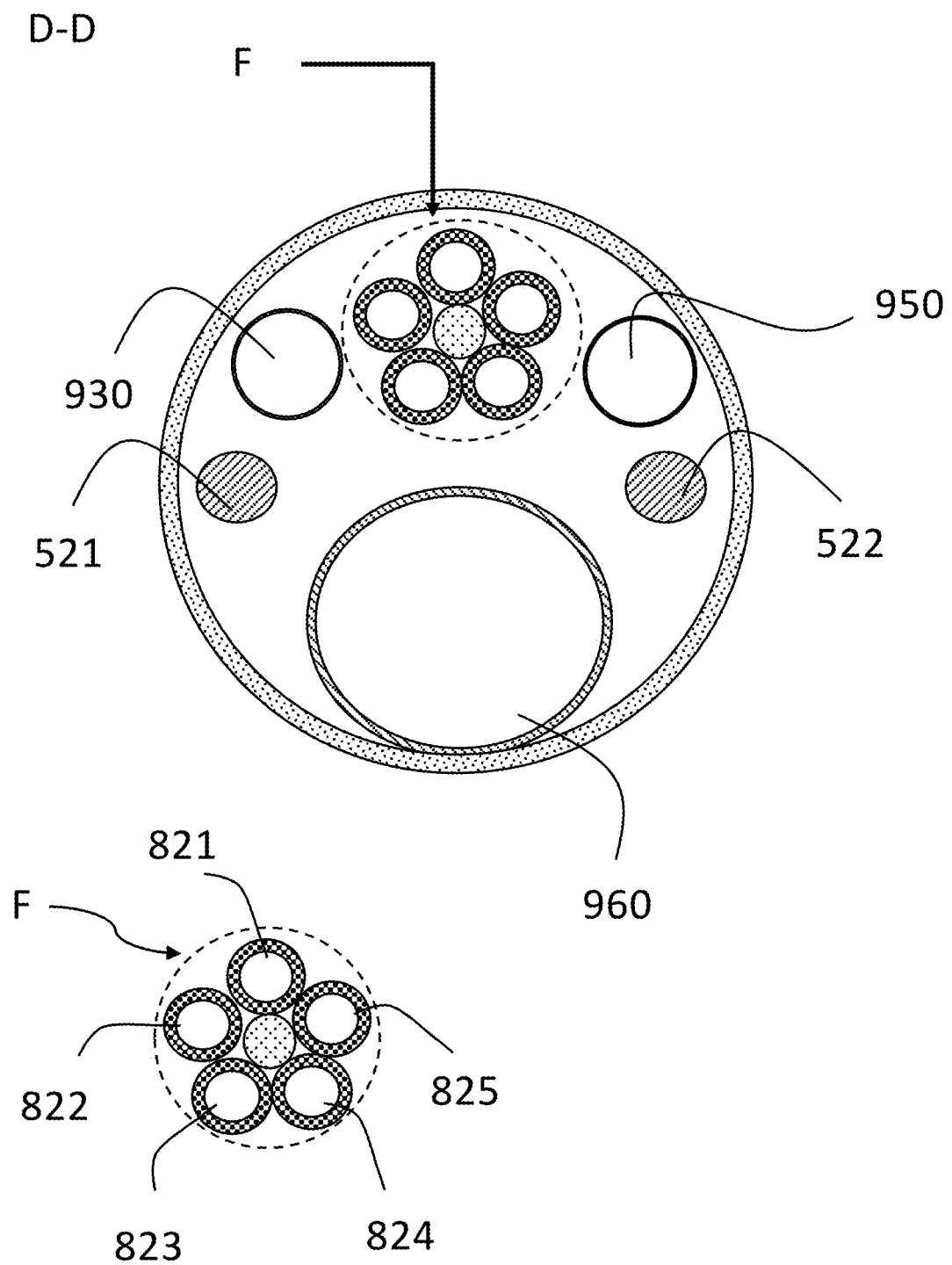
Figure 10. Present Invention

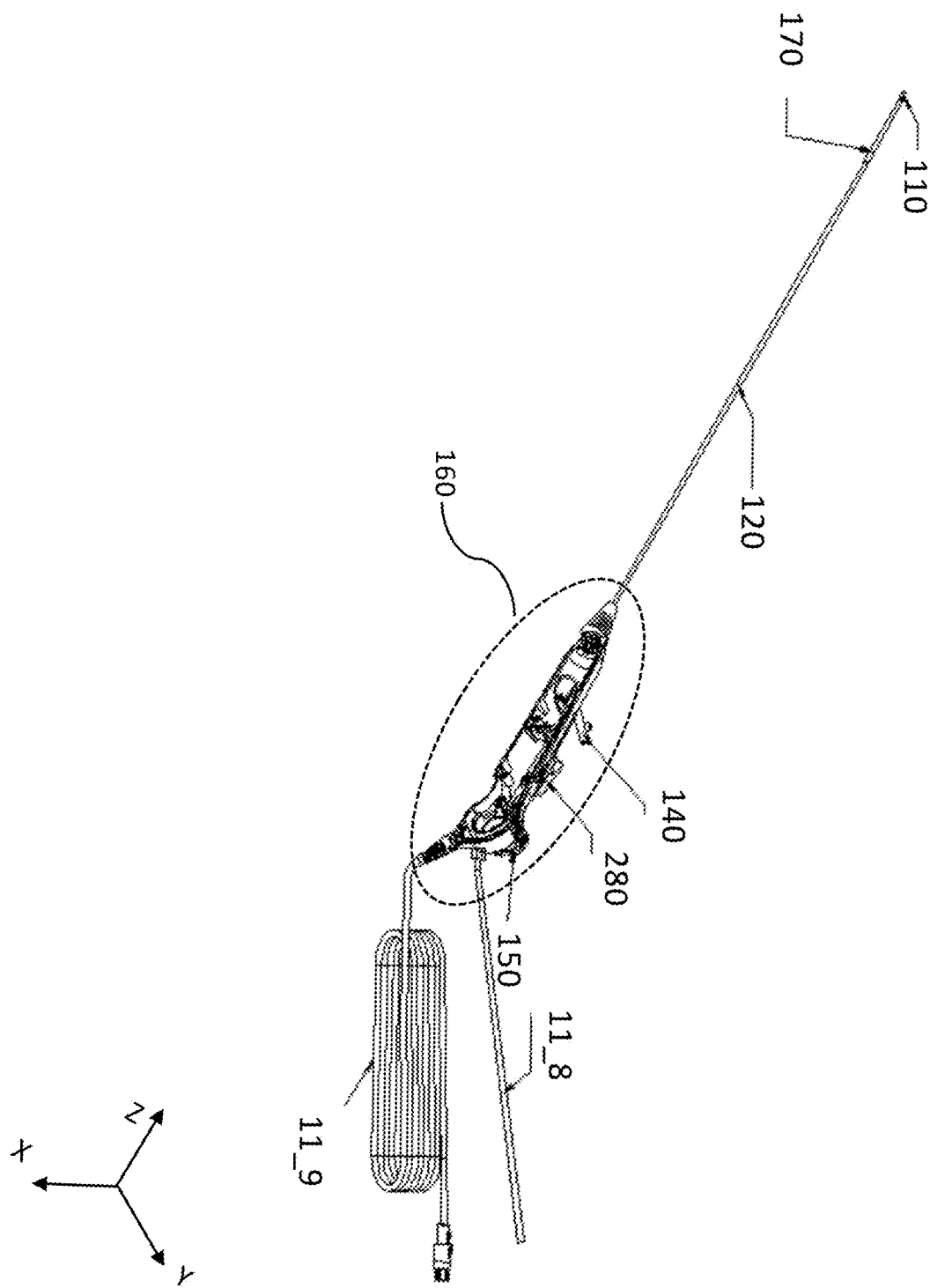
Figure 11. Present Invention

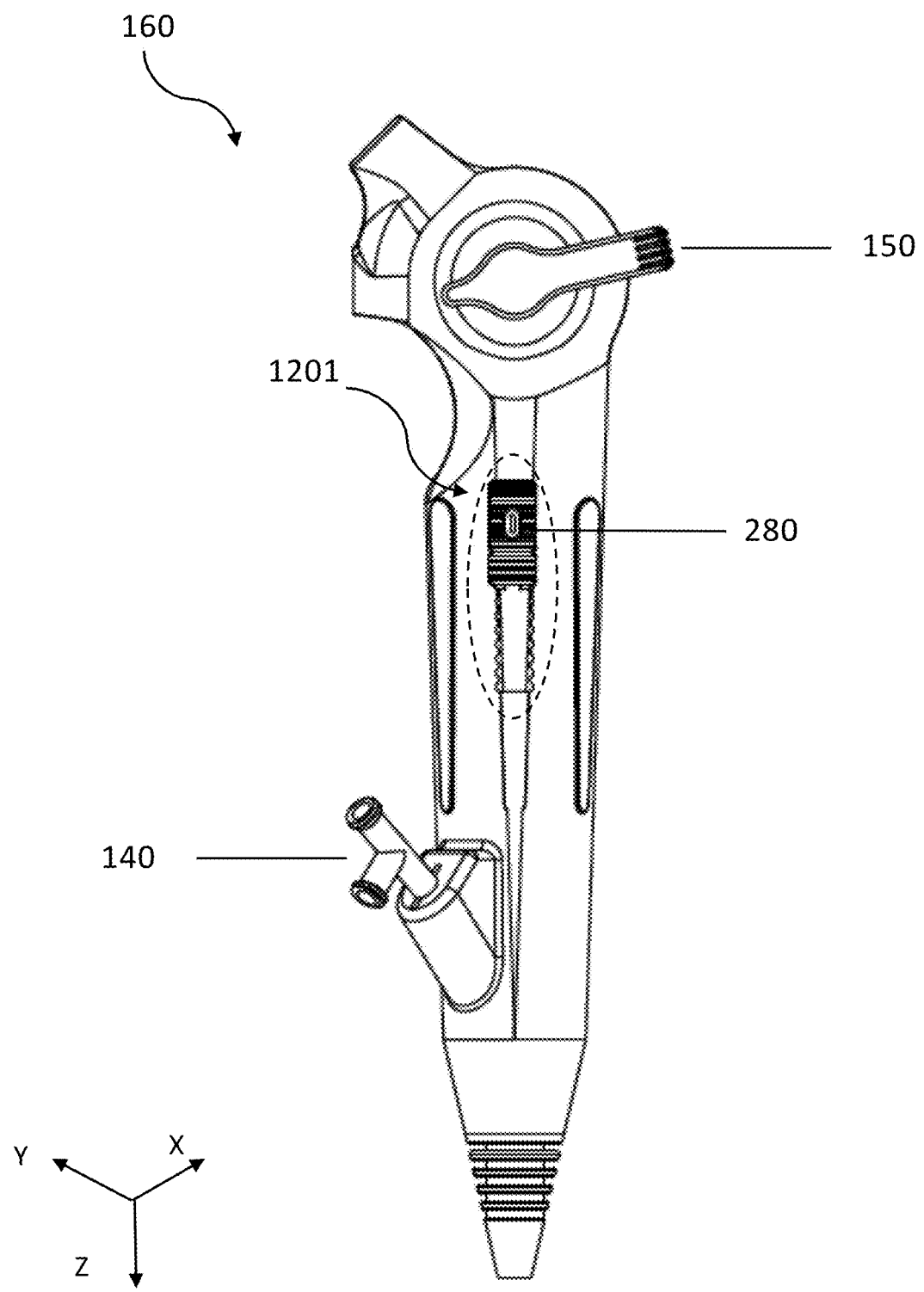
Figure 12. Present Invention

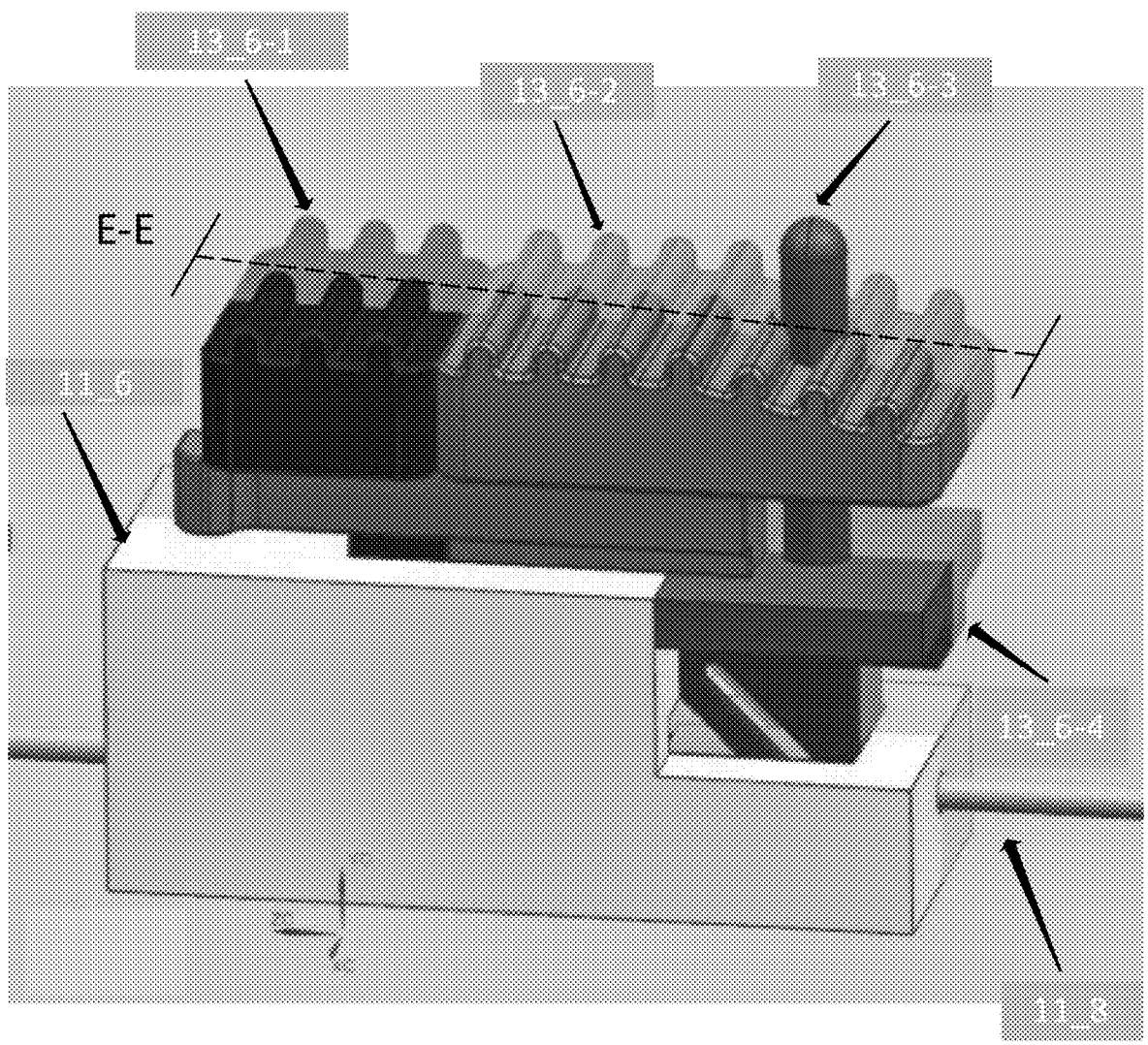
Figure 13. Present Invention

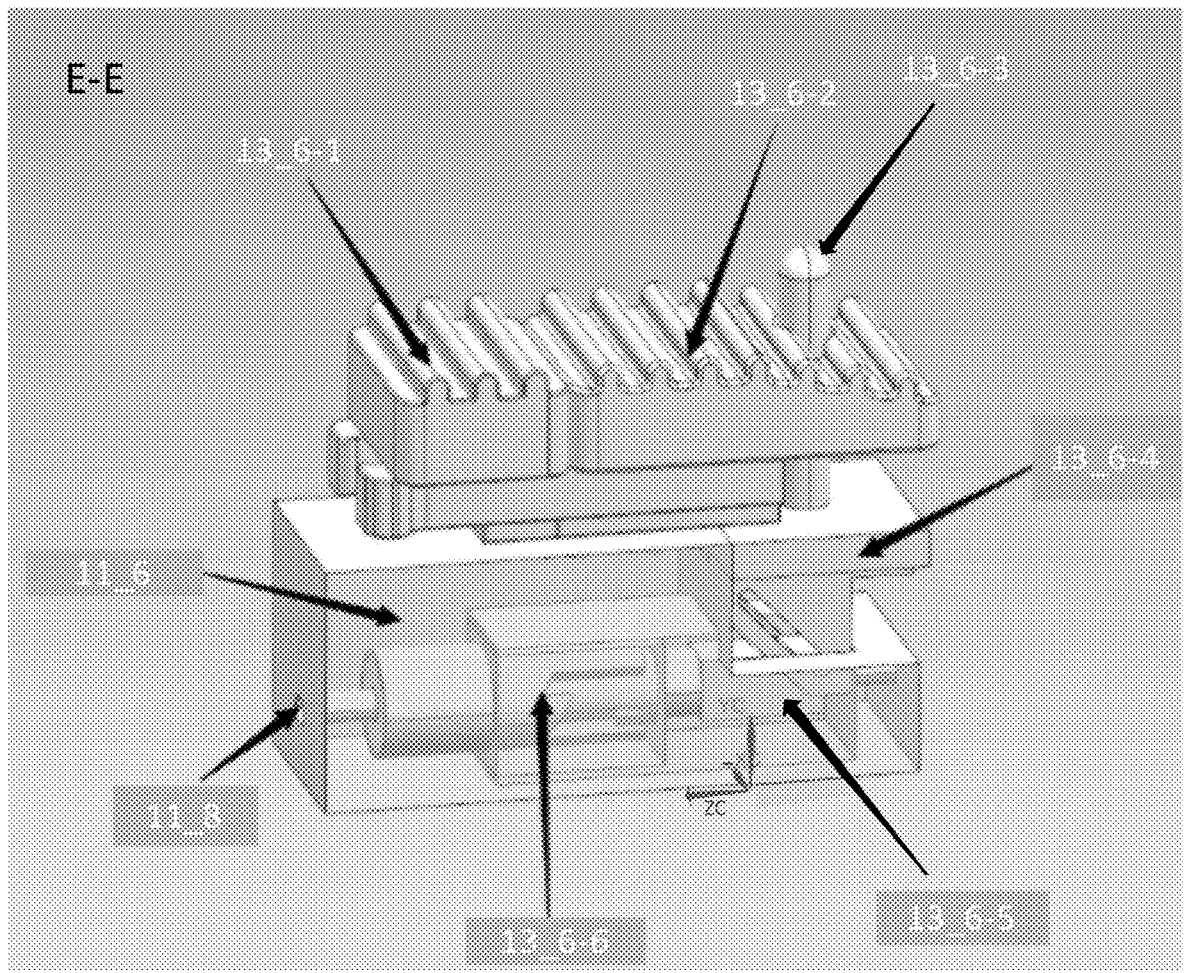
Figure 14. Present Invention

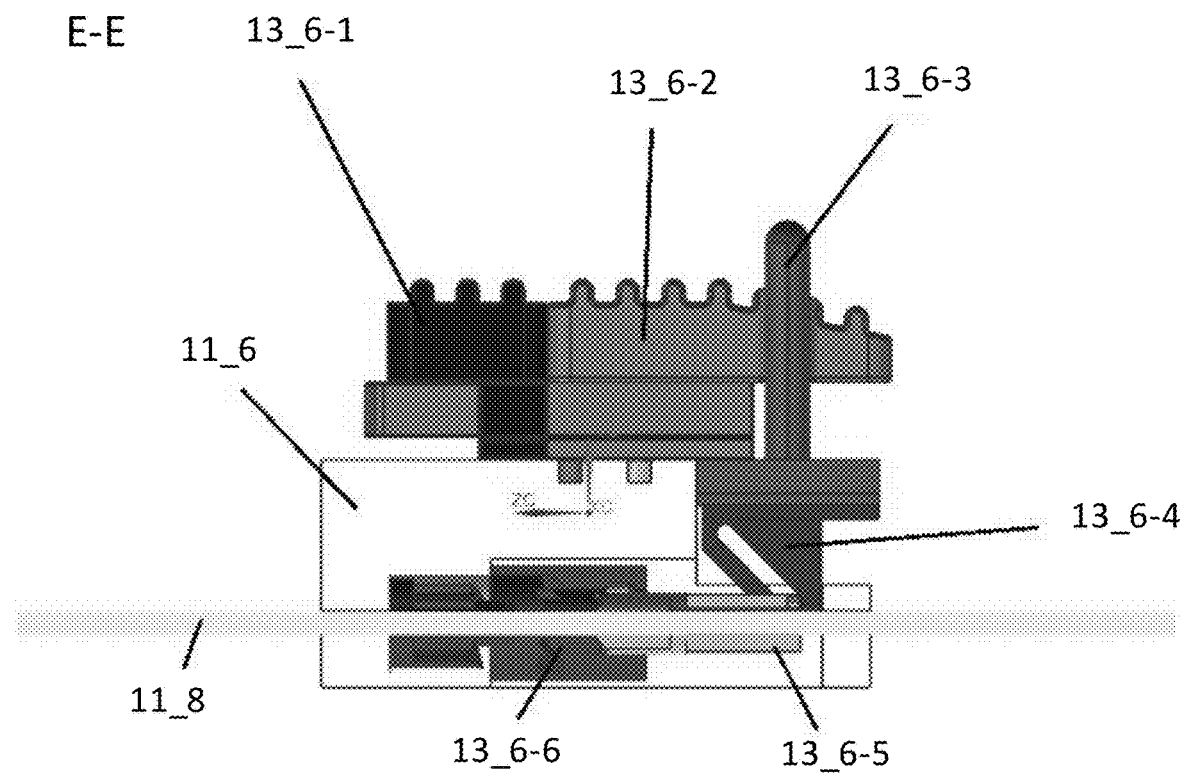
Figure 15. Present Invention

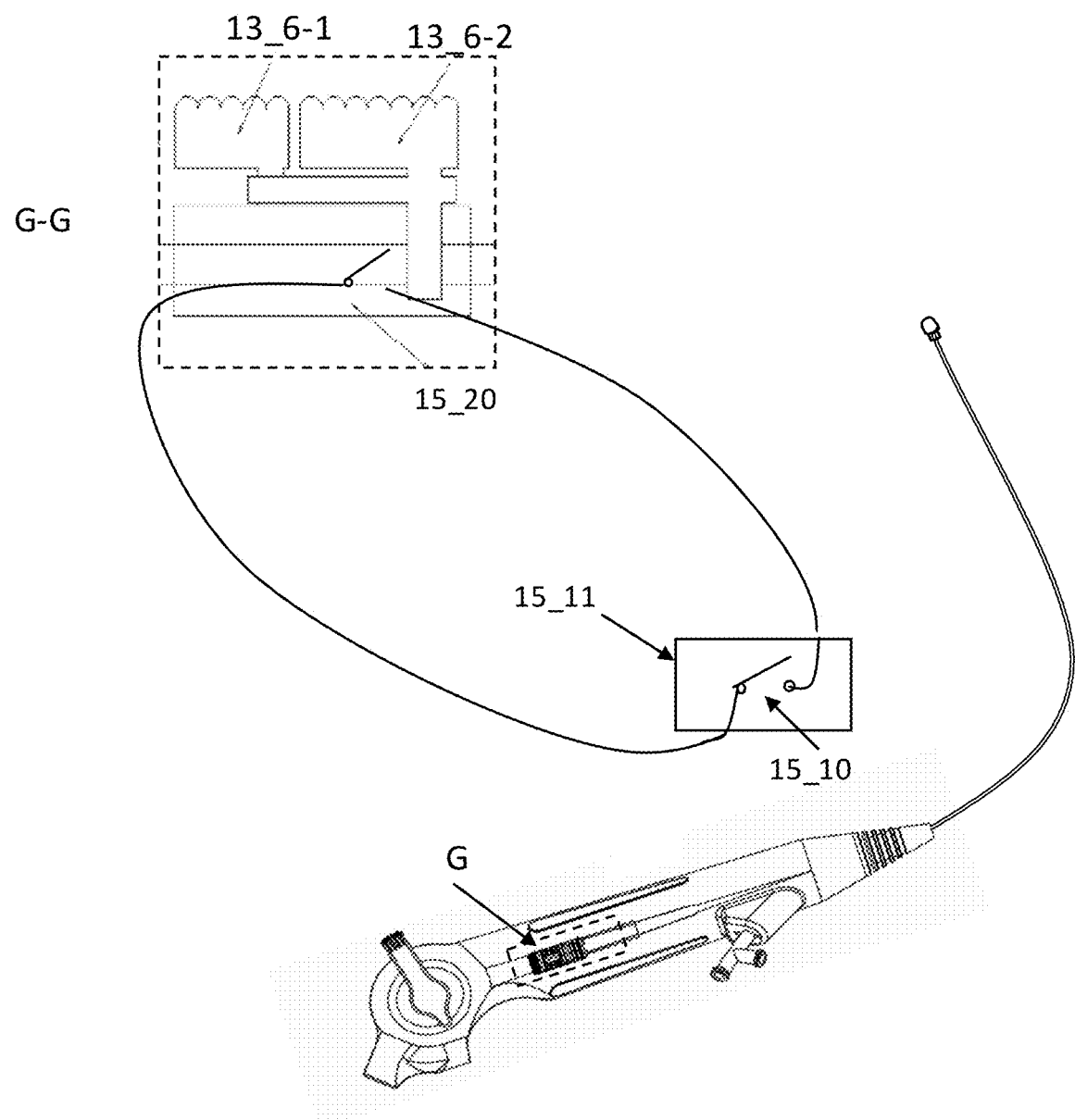
Figure 16. Present Invention

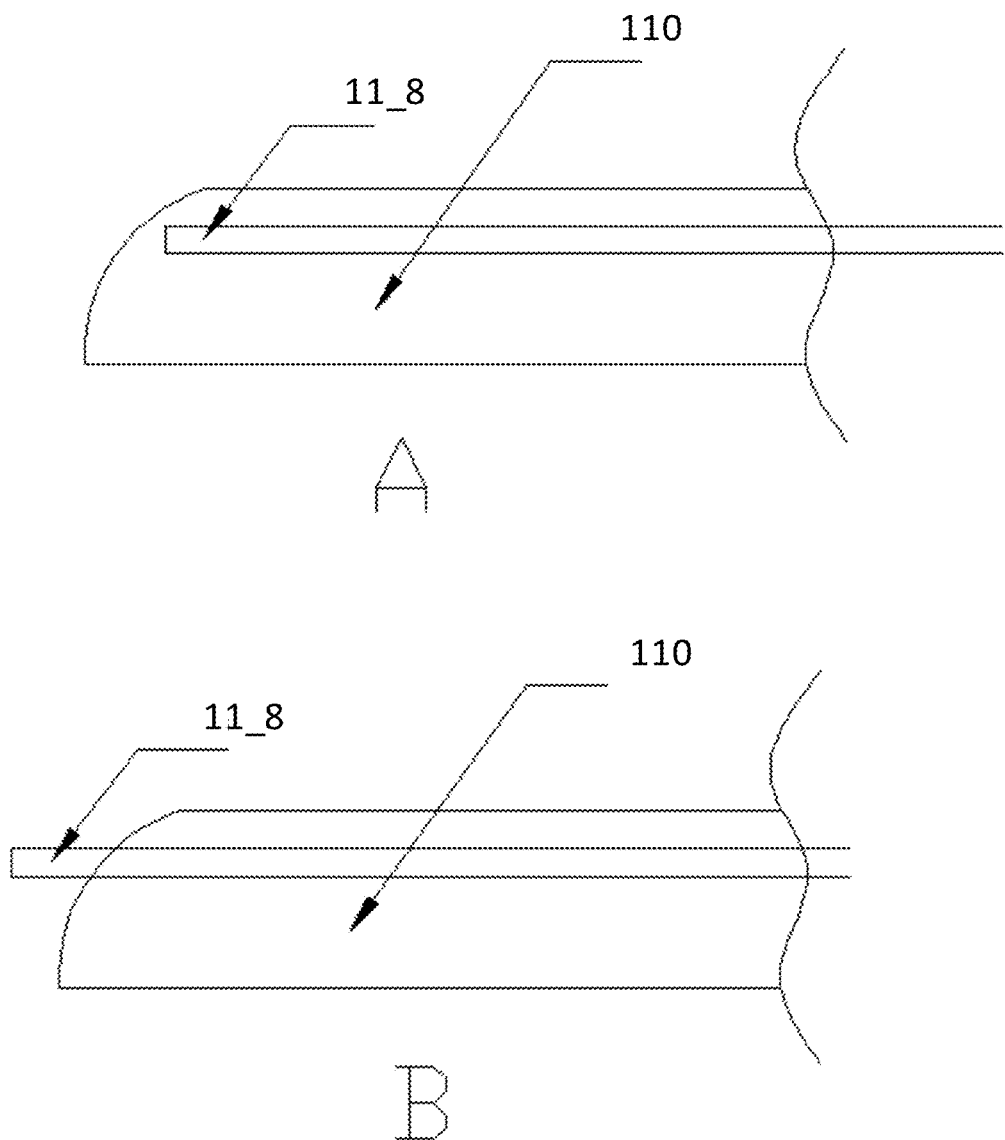
Figure 17. Present Invention

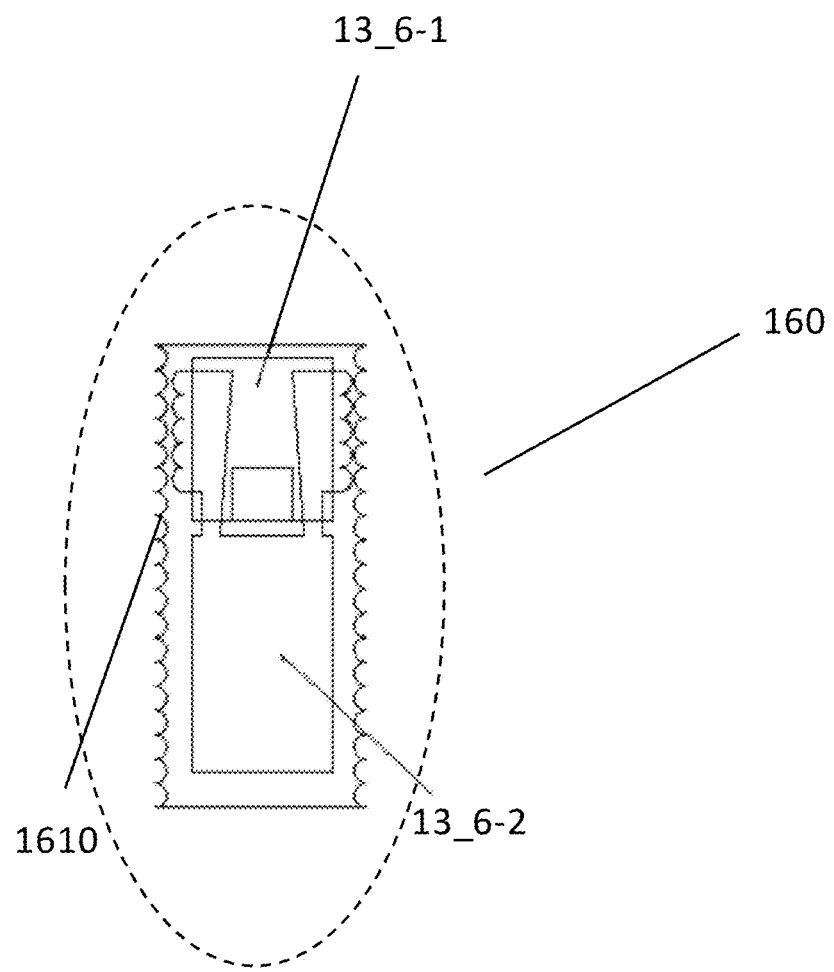
Figure 18. Present Invention

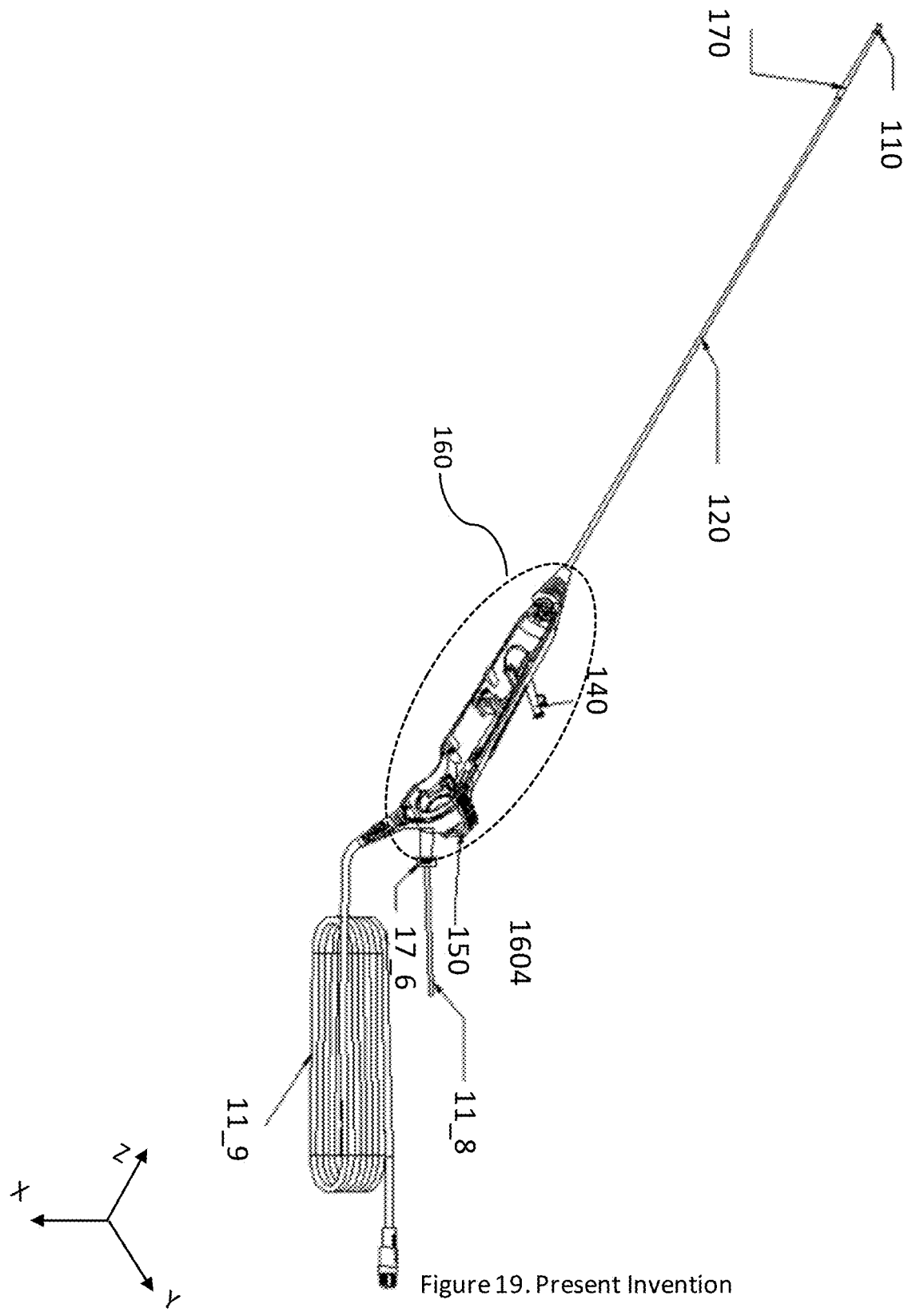
Figure 19. Present Invention

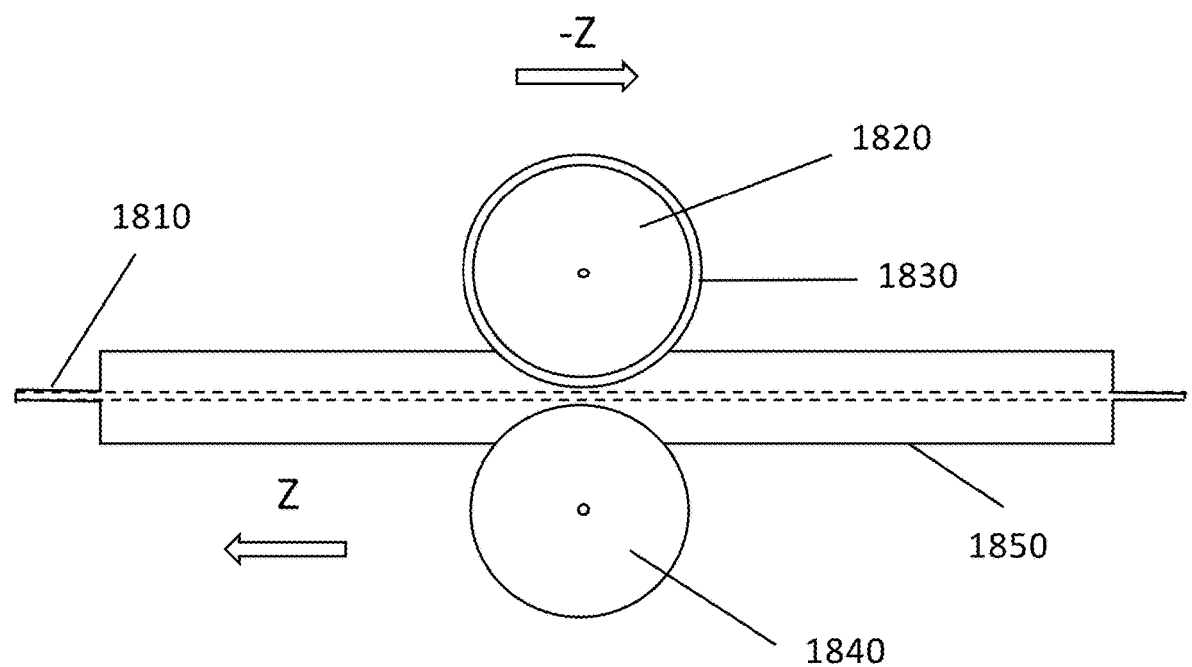
Figure 20. Present Invention

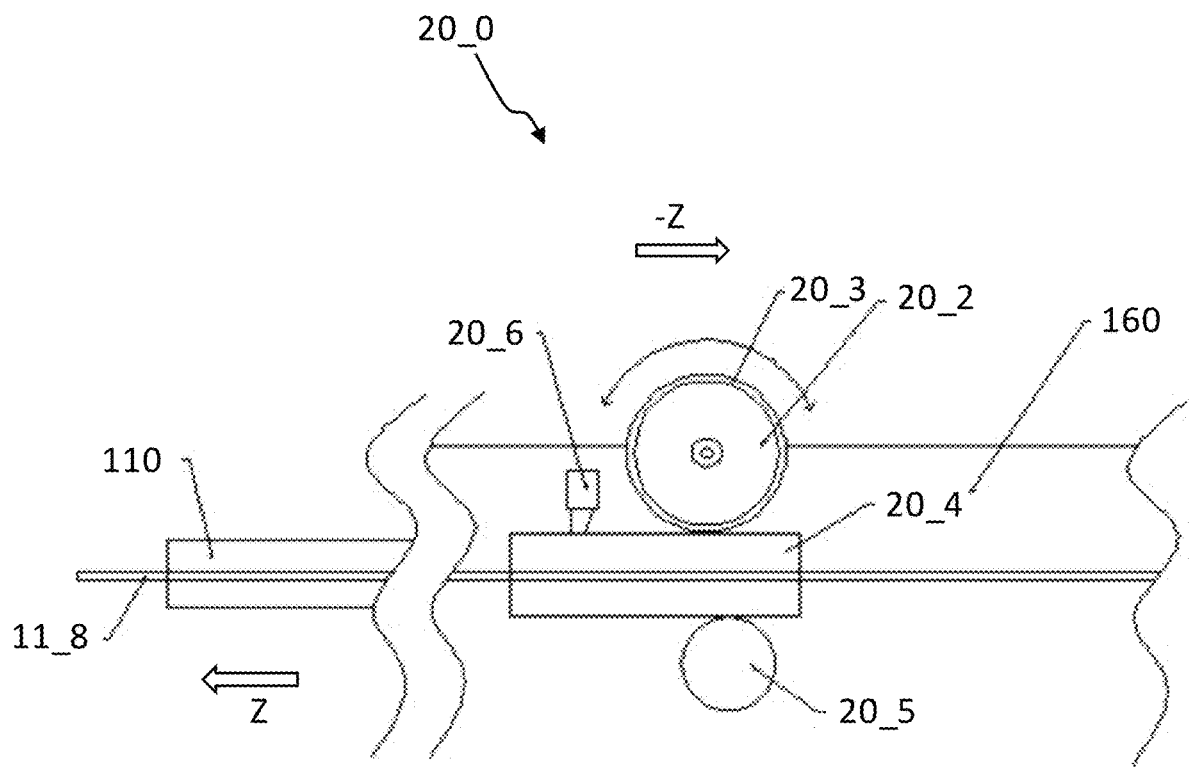
Figure 21. Present Invention

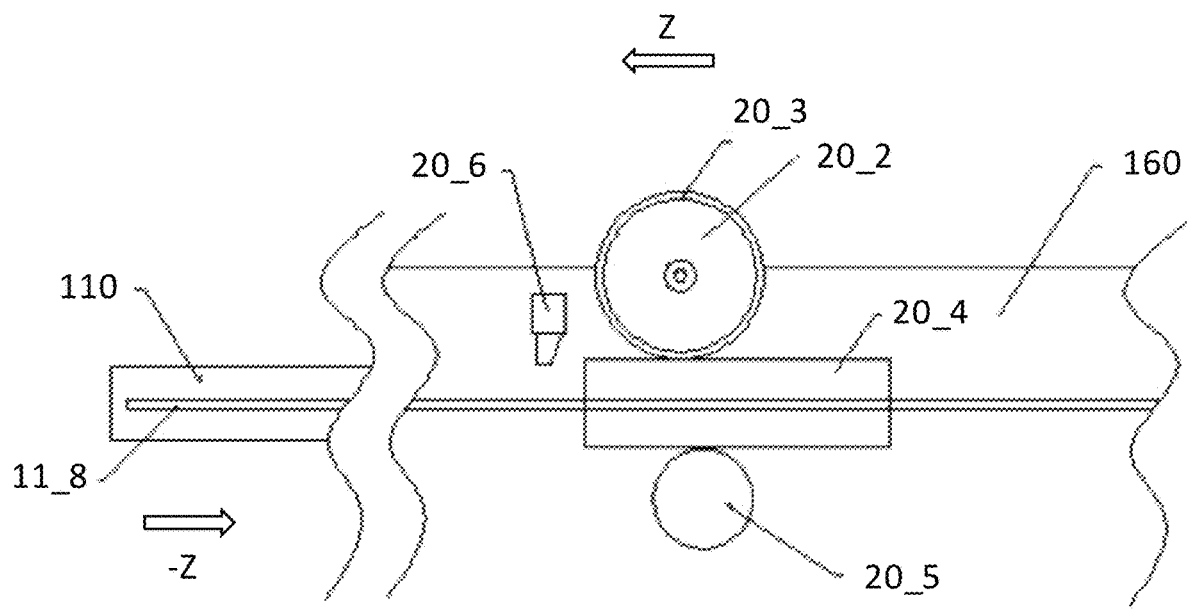
Figure 22. Present Invention

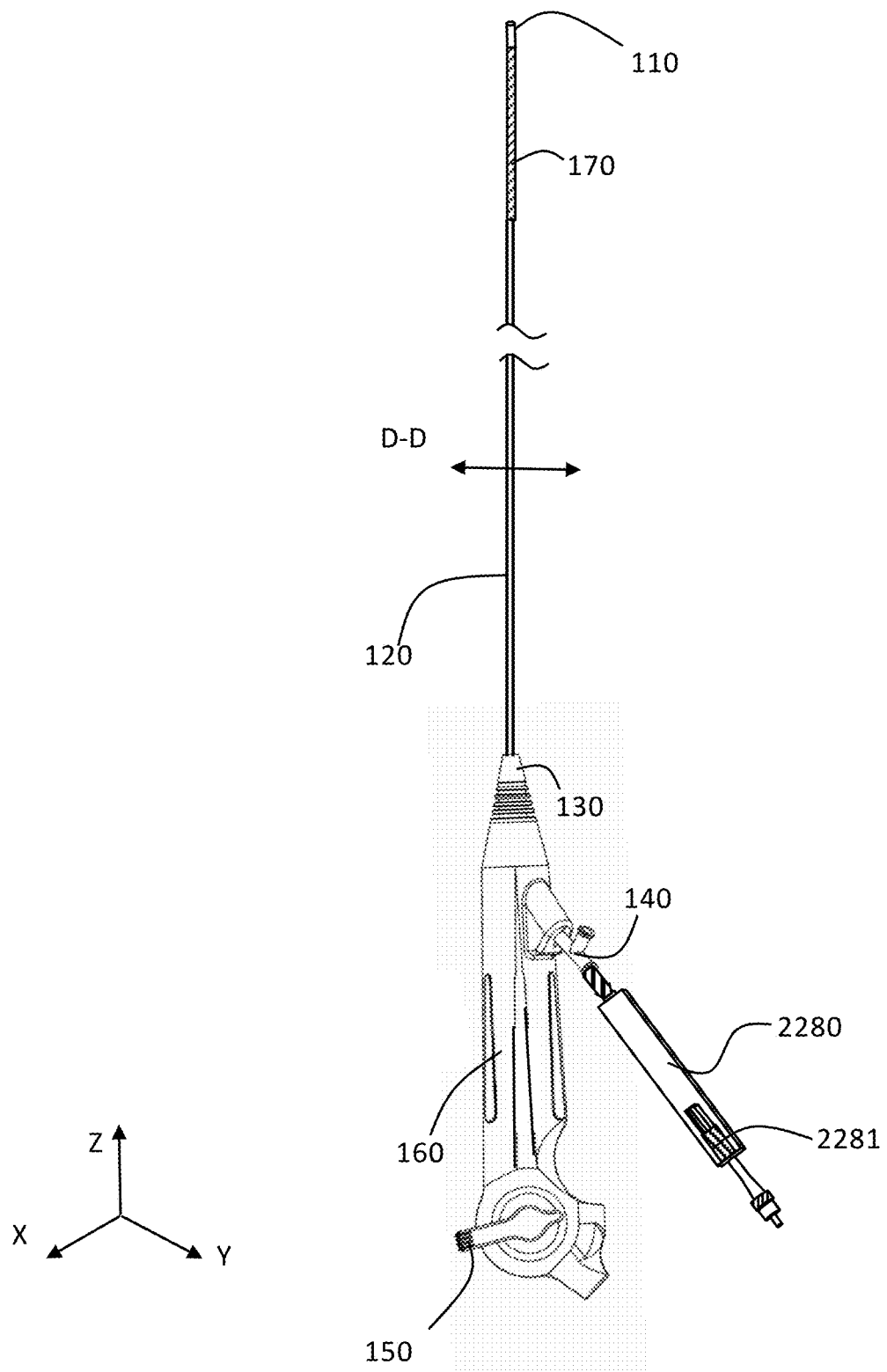
Figure 23. Present Invention

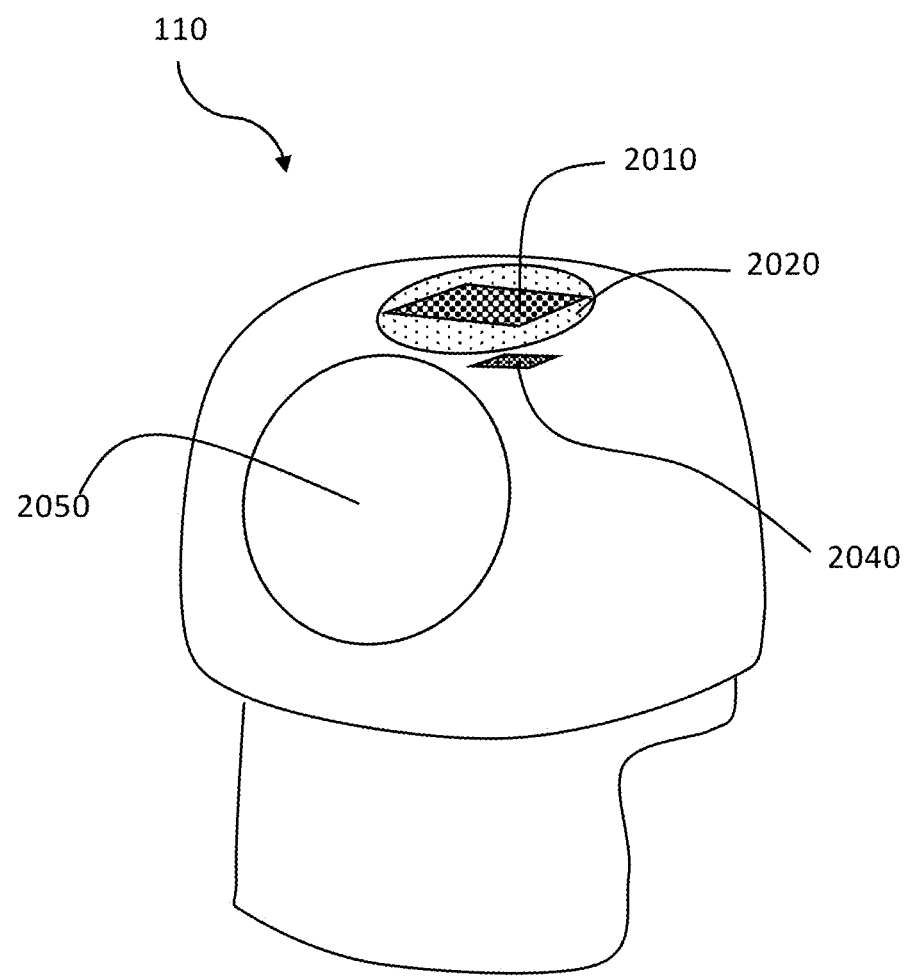
Figure 24. Present Invention

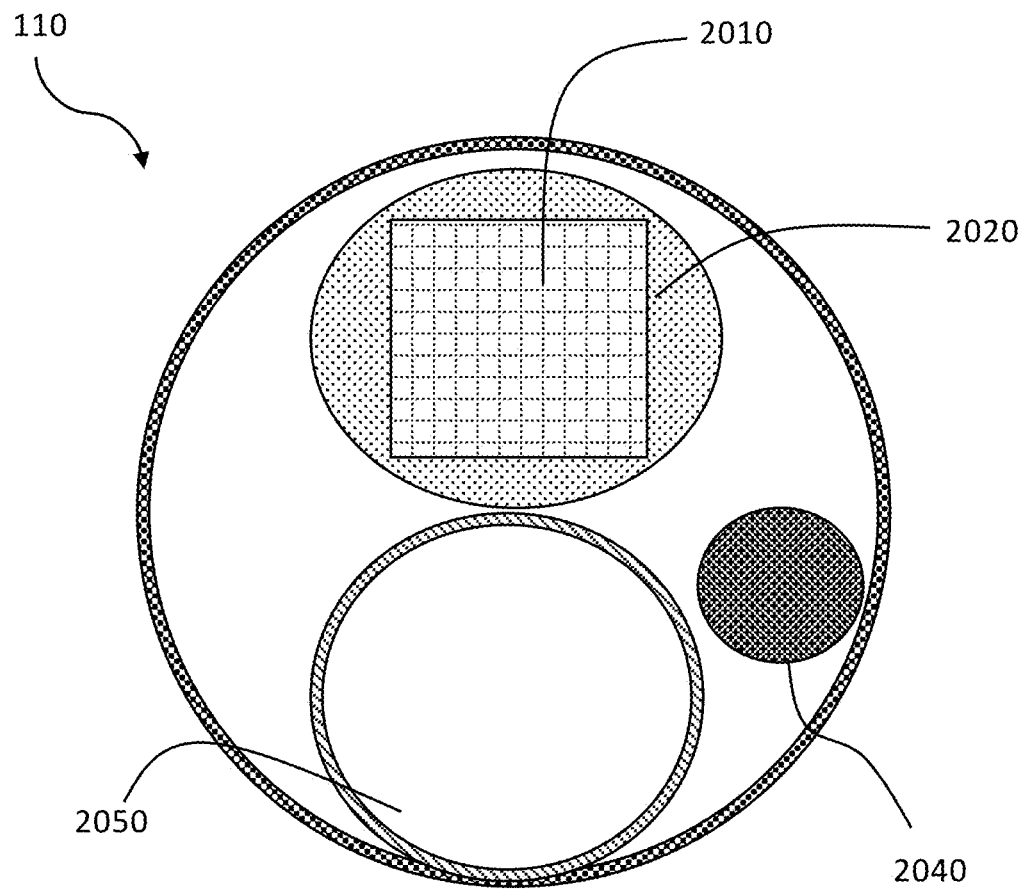
Figure 25. Present Invention

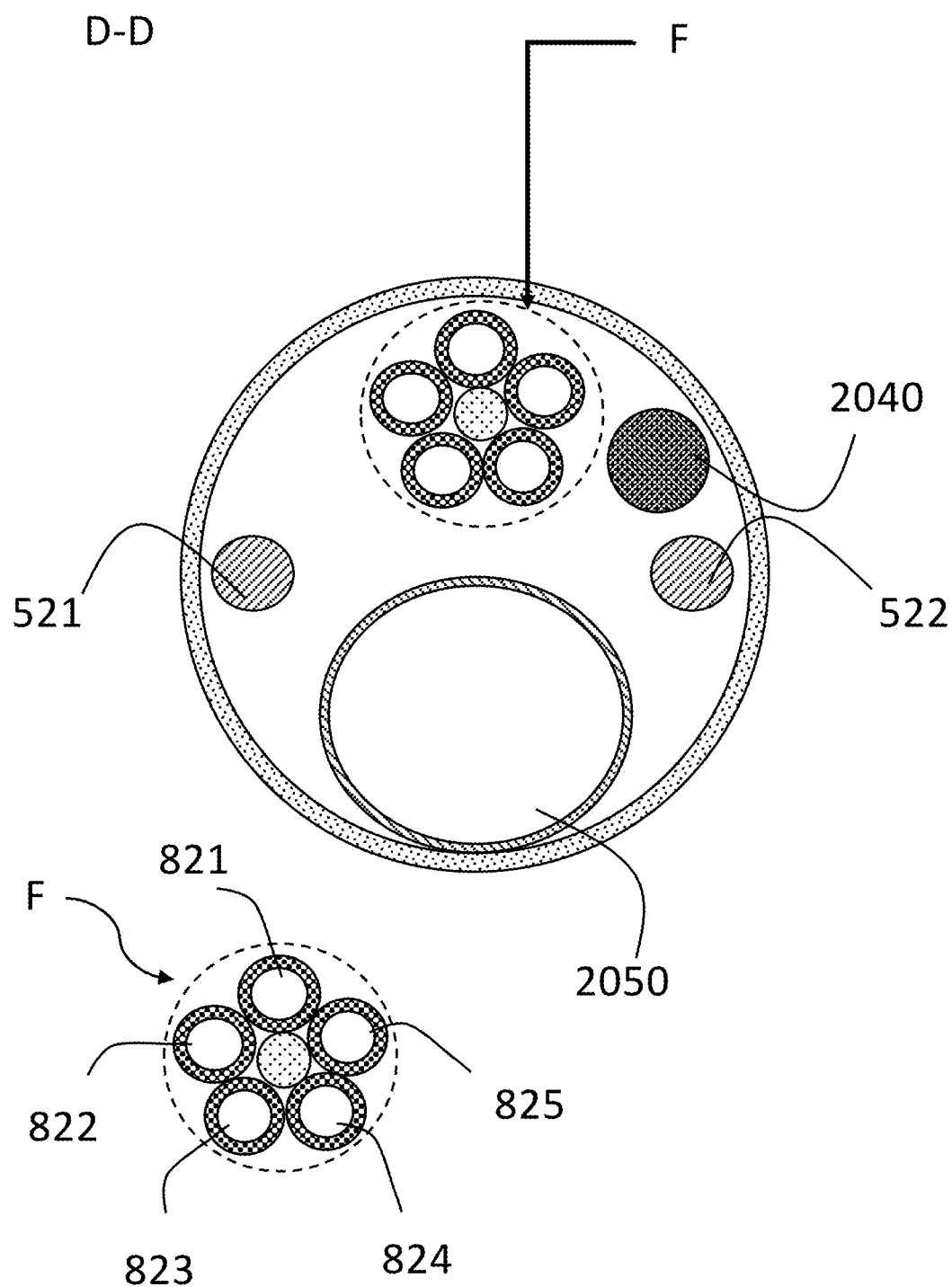
Figure 26. Present Invention

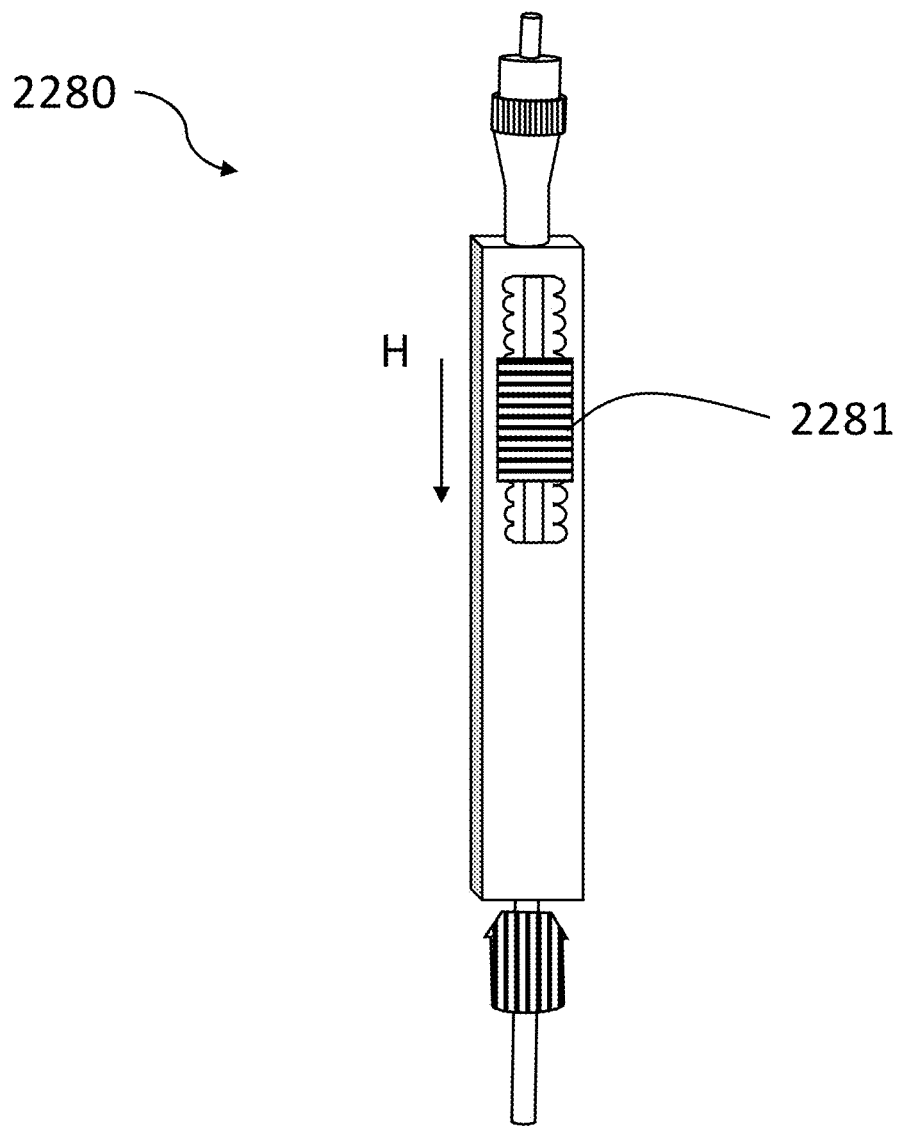
Figure 27. Present Invention

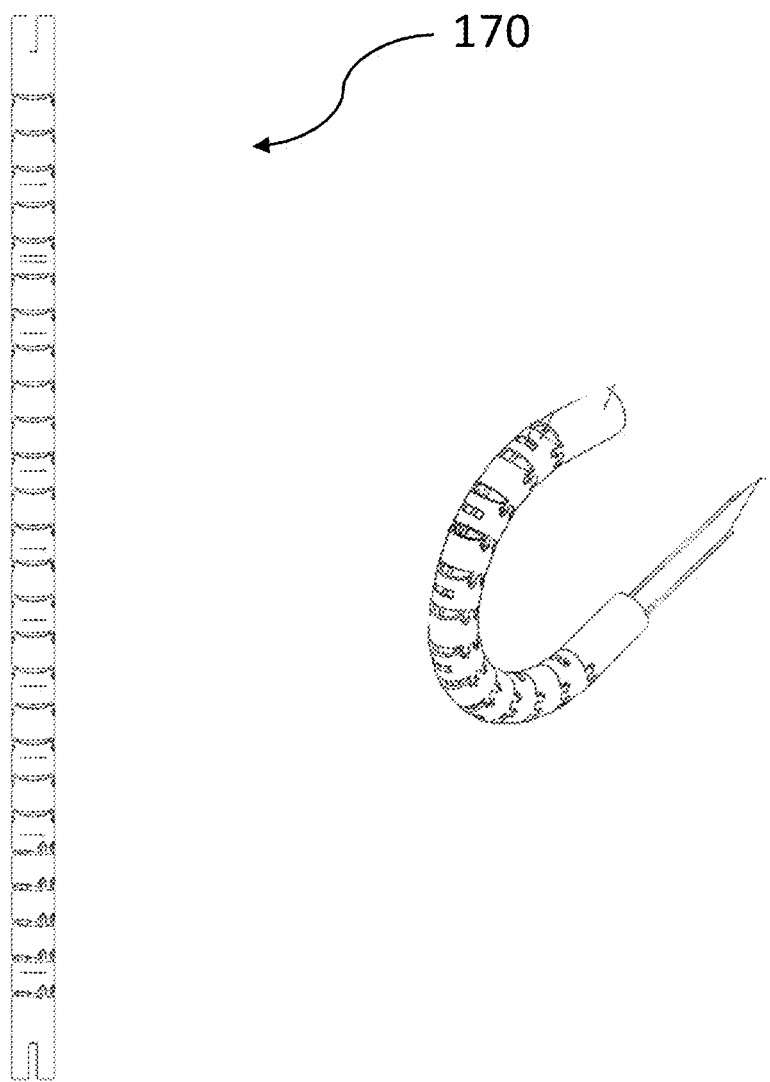
Figure 28. Present Invention

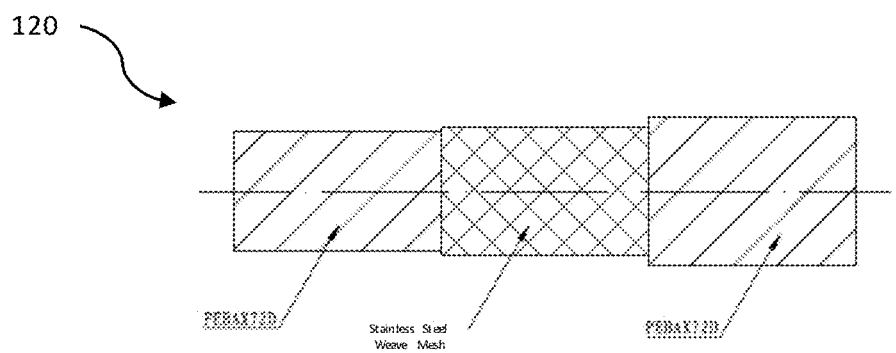
Figure 29. Present Invention

SINGLE-USE ENDOSCOPE WITH BUILT-IN OPTICAL FIBERS AND FIXTURES

RELATED APPLICATIONS

This application is a continuation-in-part (CIP) application of prior application Ser. No. 15/246,636 filed on 2016 Aug. 25.

This application is also a continuation-in-part (CIP) application of prior application Ser. No. 15/649,485 filed on 2017 Jul. 13 claiming a priority date as 2016 Nov. 24 on which both Chinese Patent Applications No. 201611041752.8 and 201611041782.9 were filed.

This application is also a continuation-in-part (CIP) application of prior U.S. application Ser. No. 15/790,914 filed on 2017 Oct. 23 and prior U.S. application Ser. No. 15/823,582 filed on 2017 Nov. 28.

This application is also a continuation-in-part (CIP) application of prior U.S. application Ser. No. 15/854,009 filed on 2017 Dec. 26.

The instant application seeks the same priorities as that of the related applications in part. The entire contents of each of which are incorporated herein by reference.

BACKGROUND OF THE INVENTION

1. Field of the Invention

The present invention belongs to a field of biomedical instrumentation. More specifically the present invention belongs to a field of endoscopes including ureteroscope, cystoscopy, gastroscopy, laparoscopy, etc. Specifications below use a ureteroscope in the present invention as an example. Similar concepts are easily extended to all types of endoscopes in general.

2. Description of the Related Art

The endoscopy is a procedure in which a physician uses a specialized instrument to observe and operate on the internal organs and vessels inside a patient's body without making large incisions. The ureteroscopy is an examination of an upper urinary tract of a patient. A ureteroscope passes through a urethra and a bladder, and into a ureter and a kidney. It is used in diagnosis and treatment of diseases, such as kidney stones that can be removed by using endoscopic accessories. A flexible ureteroscope has an actively deflectable distal end, enabling up to 170 degree angulations. The latest generation of flexible ureteroscope can bend even further up to 270 degrees by using a secondary active deflection mechanism.

BRIEF SUMMARY OF THE PRESENT INVENTION

Laser fibers are now being used routinely in many endoscopic surgeries. During a typical procedure, a surgeon usually uses one hand to hold a handle and operate an endoscope, and uses another hand to insert a laser fiber through the working channel of the endoscope. When the surgeon observes a stone/calculus in the endoscopic view, the laser fiber protrudes several millimeters from the distal-end of the endoscope, and targets the stone. The surgeon then turns on the power switch, fires the laser light, and breaks apart the stone into several smaller fragments. These fragments can be removed either from urine excretion or with the aid of accessories through the working channel, such as a retrieval basket.

However, this routine laser lithotripsy procedure still suffers from limitations. Firstly, this procedure requires two hands to operate both the endoscope and the laser fiber. Secondly, due to the size limitation of the working channel, a laser fiber cannot be used at the same time together with another surgical tool, such as a retrieval basket or a grasper, yet some complicated operations require using both instruments simultaneously. Thirdly, mis-operations of a laser fiber easily damage the electronic components at the endoscope tip, because the endoscope and the laser surgical instrument are used independently. Fourthly, a small-diameter laser fiber sways inside a relatively larger working channel while saline continuously flushes into the same channel. It results in difficulties for the laser fiber to aim at stones or calculus.

In this present invention, a special lumen is created for containing an optical fiber along the insertion tube of endoscope. An optical fiber placement device is designed and installed inside an endoscope handle to control the movements of the embedded fiber. A safety lock mechanism is added to prevent from error trigger of laser generation source. Several implementations are proposed to achieve design goals.

Firstly, the embedded laser fiber enables the one-handed operations. In this present invention, the combination of laser fibers and endoscope handle provides opportunities for surgeons to operate with other medical tools by allowing one hand to be free. Moreover, the integrated conduit keeps the fiber away from being crossed or pressed and subsequently broken by operators.

Secondly, in the present invention, a linkage between the laser device and the endoscope is proposed to prevent accidental damages to the endoscope. By clicking the retractable control stick installed in the slider, the tip of the laser fiber is extended a few millimeters ahead of the endoscope tip, and the linkage is unlocked for using the laser device. Clicking the retractable control stick again to retract the laser fiber back, and the linkage is locked to disable the use of laser.

Finally, four implementations of optical fiber placement device are proposed to control the movement of the laser fiber during operations.

This invention shows four embodiments of the optical fiber placement device, the ultra-small pressure sensor, and one or more optical fibers.

A first embodiment of the present invention has an optical fiber with sufficient length partially embedded in and along the catheter and the endoscope handle. An optical fiber placement device coupled with the endoscope handle is designed to move the optical fiber.

A second embodiment of the present invention has two optical fibers embedded in and along the catheter and the endoscope handle. An extra opening for the ultra-small pressure sensor is designed at the distal end to dynamically monitor the perfusion pressure during operations. Two optical fiber placement devices coupled with the endoscope handle are designed to move the optical fibers.

A third embodiment of the present invention has an optical fiber and an ultra-small pressure sensor embedded in and along the catheter and the endoscope handle. An optical fiber placement device coupled with the endoscope handle is designed to move the optical fiber.

For the optical fiber placement device, four implementations are illustrated. The first implementation of the optical fiber placement device has one slider installed on the side of the endoscope handle. By pushing the slider toward the distal end, the laser fiber can be extended.

The second implementation has the device designed to be detachable and can be inserted into a proximal end of the endoscope handle (the place where the control lever is located) or into the working channel. Laser fiber is embedded along the catheter and can be moved toward the distal end by using the optical fiber placement device.

The third and fourth implementation of the optical fiber placement device has two wheels placed symmetrically with respect to the laser fiber. The optical fiber moves freely inside the conduit when the drive wheel is rotated.

A fourth embodiment of the present invention has an optical fiber placement device attached to the endoscope handle at the 3-way Luer connector. The laser fiber including its ETFE jacket is placed through the Luer connector and then the working channel. An ultra-small perfusion pressure sensor is embedded along and in the catheter and is connected to an external sensing process device through the endoscope handle.

BRIEF DESCRIPTION OF THE DRAWINGS

FIG. 1 illustrates a prior art of an endoscope.
FIG. 2 illustrates the assembly drawing of the present invention.
FIG. 3 illustrates a general view of the present invention.
FIG. 4 illustrates a view of the distal end along the −Z direction.
FIG. 3 illustrates a general view of the present invention.
FIG. 5 illustrates a sectional view of the bend portion.
FIG. 6 illustrates a general view of the distal end.
FIG. 7 illustrates a view of the distal end along the −Z direction.
FIG. 8 illustrates a sectional view of the catheter.
FIG. 9 illustrates a view of the distal end along the −Z direction.
FIG. 10 illustrates a sectional view of the catheter.
FIG. 11 illustrates the first implementation of the optical fiber placement device.
FIG. 12 illustrates a view of the endoscope handle.
FIG. 13 illustrates a 3d view of the optical fiber placement device.
FIG. 14 illustrates a 3d sectional view of the optical fiber placement device along the direction E-E.
FIG. 15 illustrates a supplementary drawing of optical fiber placement device with respect to the FIG. 14.
FIG. 16 illustrates the structure of safety switch.
FIG. 17 illustrates a view of distal end when the optical fiber placement device is in use.
FIG. 18 illustrates a view of the slider along the −Y direction in an X-Y-Z Cartesian coordinate.
FIG. 19 illustrates the second implementation of the optical fiber placement device.
FIG. 20 illustrates the third implementation of the optical fiber placement device.
FIG. 21 illustrates the fourth implementation of the optical fiber placement device (Operational Mode).
FIG. 22 illustrates the fourth implementation of the optical fiber placement device (Non-operational Mode)
FIG. 23 illustrates a general view of the endoscope with an external optical fiber placement device.
FIG. 24 illustrates the distal end of the fourth embodiment.
FIG. 25 illustrates a view of the distal end along the −Z direction.

FIG. 26 illustrates a sectional view of the catheter.
FIG. 27 illustrates an external optical fiber placement device.
FIG. 28 illustrates the structure of bend portion.
FIG. 29 illustrates the structure of catheter.

DETAILED DESCRIPTION OF THE INVENTION

The following description with reference to exemplary and illustration drawings of the present invention will be further described in detail, but the present illustration is not intended to limit the embodiment of the present invention, any similar structure of the present invention and similar changes should be included in the scope of the present invention.

FIG. 1 illustrates a prior art of an ureteroscope. The endoscope has a handle (160), a 3-way Luer connector (140), a control lever (150), a strain relief (130), a catheter (120), a bend portion (170) and a distal end (110).

Calculi, stone, and similar lesions inside human body can be fragmented by holmium laser, and a laser fiber is used to conduct laser energy to the targets.

The ureteroscope is used by physicians to access, to visualize, and perform procedures in the urinary tract. The ureteroscope enables delivery and usage of accessories such as biopsy forceps, guide wires, graspers and retrieval baskets at a surgical site. The distal end (110) of the ureteroscope articulates to 275 degrees in two directions, and the distal end (110) can be rotated a total of 360 degrees by rotating the handle (160).

The laser fiber (s) is (are) pre-installed along the conduit as well as the handle in the first three embodiments. The movements of these embedded fibers are controlled by the optical fiber placement devices. Four implementations of the device are introduced in detail. Finally, a fourth embodiment is presented with an external optical fiber placement device enters through the working channel to extend the laser fiber.

The assembly drawing of the present invention illustrated in FIG. 2 comprises a pressure spring (201), a wire wheel (202), a fixed plate for PCB (203), a PCB (204), a fiber module (205), a tip (210), a strain relief (130), a Luer joint (140) and a control lever (150). The handle is divided into two parts: the left part (260A) and the right part (260B). A slider (280) is installed on one side of the handle (260A or 260B). The laser fiber can be pushed towards the distal end (110) by sliding the slider (280).

Two separate connectors (207 & 208) are used in the present invention. The first one (207) connects the fiber module and the other one (208) connects the camera module.

FIG. 3 illustrates a general view of the endoscope with an embedded placement device. (110) is the distal end of the endoscope and (170) is the bend portion of the catheter (120).

FIG. 4 and FIG. 5 illustrate the details of the first embodiment of the present invention.

FIG. 4 is a view of the distal end along the direction −Z. The lighting sources (420A) and (420B) are symmetric with respect to the image sensor (410) covered by a lens. The working channel opening (450) is under the image sensor and the lighting source (420A & 420B). The laser fiber (431) is placed at a proper location.

The lighting sources (420A) and (420B) are selected from μLED/OLED/infrared LED/Laser LED/Laser diode/LED/optical fiber with suitable size(s), shape, intensity, and other desired parameters.

FIG. 5 is the sectional view of the bend portion (170). A pair of steel wire (521 & 522) are placed symmetrically along the vertical axis of the working channel (450). (510) is the channel reserved for electric cables and (431) is designed for the fiber conduit.

Suitable tool(s) can extend through the working channel (450) to perform at the target area.

In this embodiment, fibers can reach the distal end (110) through specific conduits other than the working channel (450). Other surgical tools can enter the catheter (120) through the working channel (450) to assist the fragmentation of lesions.

The shell of the distal end (110) is manufactured through injection molding, with a mix of polymer composite material.

A second embodiment of the present invention shown in FIG. 6, FIG. 7 and FIG. 8 is composed of two fiber conduits, an image sensor surrounded by lighting sources, a working channel and an ultra-small pressure sensor.

FIG. 6 illustrates the distal end (110) in detail. The distal end (110) is wedge-shaped and comprises a working channel opening (650), a first laser fiber opening (631), a second laser fiber opening (632), an image sensor (610), an illumination lens (620) and an ultra-small pressure sensor (640). Two laser fiber openings are symmetric with respect to the image sensor (610).

A vertical view of the distal end (110) along the direction −Z is shown in FIG. 7. The lighting source (620) is designed to surround the image sensor (610) covered by a lens. The working channel opening (650) is placed adjacent to the image sensor (610) as well as the lighting source (620). The ultra-small pressure sensor (640) is placed at a proper location.

The lighting source (620) is selected from µLED/OLED/infrared LED/Laser LED/Laser diode/LED/optical fiber with suitable size(s), shape, intensity, and other desired parameters.

FIG. 8 is a sectional view of the catheter (120) along direction −Z at position D-D. The six-wires bundle (F) is composed of two coaxial cables and three wires. Two coaxial cables are designed for XVCLK (821) and VOUT (822) while three wires are reserved for VDD (823), LED+ (824) and LED−(825). A pair of steel wire (521 & 522) are placed symmetrically along the vertical axis of the working channel (650). The steel wires (521 & 522) connect the bend portion (170) with the control lever (150) to change the bending direction of the bend portion (170). Two fiber conduits (631 & 632) are placed symmetrically along the vertical axis of the working channel (650). The diameter of two fiber conduits (631 & 632) are designed variously depending on the diameter of the desired fiber. The ultra-small pressure sensor (640) is placed at a proper location.

The inner surfaces of the fiber conduits (631 & 632) are treated properly to make the fibers move smoothly inside without breakage or knots.

In this embodiment, two laser fibers are pre-installed in the endoscopic. Two optical fiber placement devices coupled with the endoscope handle are applied to move the fibers freely inside the embedded conduits. Other surgical tools can enter the catheter via the 3-way Luer connector (140) to assist the fragmentation of lesions. A pressure sensor is embedded along the handle and the catheter to monitor the pressure during the operation.

The shell of the distal end (110) is manufactured through injection molding, with a mix of polymer composite material.

FIG. 9 and FIG. 10 introduce a third embodiment of the present invention. In this embodiment, a laser fiber as well as an ultra-small pressure sensor are pre-installed in the handle. The tip of the laser fiber can be replaced easily by sliding the slider (280) toward the distal end (110). The slider (280) is installed on one side of the handle.

FIG. 9 illustrates a view of the distal end (110) along the direction −Z. The lighting source (940) is designed to surround the image sensor (920) covered by a lens. The working channel opening (960) lies adjacent to the image sensor (920) and the lighting source (940). An ultra-small pressure sensor (950) is placed opposite a laser fiber (930).

FIG. 10 is the sectional view of the catheter. The six-wires bundle (F) is designed for XVCLK (821), VOUT (822), VDD (823), LED+(824) and LED− (825). A pair of steel wire (521 & 522) are placed symmetrically along the vertical axis of working channel (960) to change the bending direction of the bend portion (170). Two conduits, one for optical fiber (930) and the other for pressure sensor (950), are placed symmetric with respect to the vertical axis of working channel (960).

In this embodiment, one laser fiber and one ultra-small pressure sensor are embedded along the catheter and the endoscope handle. A slider (280) is designed and installed on one side of the handle to control the movement of the laser fiber. In case of the tip of the laser fiber is broken, shift the slider toward the distal end to keep the broken tip a few millimeters above the distal end, and then the damaged part can be cut off easily.

The first three embodiments introduced above have at least one optical fiber with sufficient length partially embedded in and along the conduit and the endoscope handle. These optical fiber(s) are movable bi-directionally along the catheter by using one or more optical fiber placement device coupled with or inside the handle. Four implementations of optical fiber placement device are presented in the following section in detail.

FIG. 11 illustrates the first implementation of the optical fiber placement device. The endoscope comprises a distal end (110), a bend portion (170), a catheter (120), a handle (160) with a slider (280) installed on, a control lever (150), a laser fiber (11_8), and an electric cable (11_9). The optical fiber placement device is built inside the endoscope handle and a slider (280) placed on the side of the handle (160) is used to control the movement of the laser fiber (11_8).

FIG. 12 illustrates the endoscope handle in detail.

FIG. 14 is the 3D sectional view of the optical fiber placement device with the cutting plane (E-E) shown in FIG. 13. An optical fiber placement device is composed of an optical fiber lock (13_6-1), an optical fiber slider (13_6-2), a retractable control stick (13_6-3), an optical fiber box (11_6), an optical fiber holder (13_6-5), a coupler (13_6-4), an axial cam (13_6-6) and a laser fiber (11_8).

In this implementation, the optical fiber box (11_6) is built inside the endoscope handle and an optical fiber holder (13_6-5), which holds a section of the optical fiber, is movable in Z and −Z directions. Both optical fiber slider (13_6-2) and optical fiber lock (13_6-1) are slid-able in Z and −Z directions and are positioned outside a housing of the endoscope handle. A coupler (13_6-4) is applied to connect the retractable control stick (13_6-3) with the optical holder (13_6-5).

While in use, the optical fiber lock (13_6-1) is slid to a position combing and joining the optical fiber slider (13_6-2), the laser fiber (11_8) is unlocked and is movable in either Z or −Z direction following the movement of optical fiber slider (13_6-2). When the fiber is placed at a proper position, the optical fiber lock (13_6-1) is separated from the optical fiber slider (13_6-2) and a bendable part of the slider will be pushed wide open against a rugged side wall of an opening (1201) of the handle (160) to lock the slider (13_6-2).

A retractable control stick (13_6-3), perpendicularly going through the slider, is movable in both Y and −Y direction. The axial cam (13_6-6) provides a bi-stable system where in one position the laser fiber is retracted (FIG. 17, A) and in the other it is protruded (FIG. 16, B). If the retractable control stick (13_6-3) is pressed once in −Y direction, the coupler (13_6-4) connecting the retractable control stick (13_6-3) to the optical holder (13_6-5) pushes the holder (13_6-5) toward the cam (13_6-6), leading the safety switch (15_20), shown in FIG. 16, remained on. The optical fiber will be protruded a few millimeters above the distal end (110) and the endoscope is in the operating state at this time. By turning on the switch of the laser generation source (15_10), the laser fiber (11_8) is activated safely to avoid the damaging the image sensor and other components of endoscope.

Pressing the retractable control stick (13_6-3) another time in −Y direction can move the laser fiber (11_8) backward and disconnect the safety switch (15_20). The usage of the safety switch prevents the laser generation source (15_11) from being turned on accidently.

FIG. 15 is the sectional view of the optical fiber placement device.

FIG. 16 illustrates the structure of the linkage, comprising a safety switch (15_20), a laser generation source (15_11) and an external laser switch (15_10), in detail.

FIG. 17 shows the retracted state (A) and the extended state (B) of the laser fiber (11_8).

FIG. 18 illustrates a view of the slider along the −Y direction in an X-Y-Z Cartesian coordinate. (13_6-1) is an optical fiber lock and (13_6-2) is an optical fiber slider. One or more pairs of coupled teeth (1610) wherein a set of teeth is built on edges of the optical fiber lock (13_6-1) and another set of teeth is built on edges of portions of the endoscope handle.

In the first implementation, the optical fiber placement device is partially built inside the endoscope handle. A special opening (1201) is reserved for the fiber placement device and a slider (280) is placed outside a housing of the handle (160) to control the movement of laser fiber.

FIG. 19 illustrates the second implementation of the optical fiber placement device. The optical fiber placement device is built as a detachable device that can be inserted into a proximal end of the endoscope handle or into a proximal end of the working channel.

The mechanical principles of the optical fiber placement device in this implementation are the same as what were described in the first implementation.

In the present implementation, the optical fiber placement device is independent from the handle and can be inserted into either the proximal end of the handle or the working channel. By pressing the control button, the embedded fiber can be extended to a suitable length and the broken tip can be easily removed.

The third implementation of the optical fiber placement device is shown in FIG. 20. A soft rubber outer wheel (1830) in which a hard plastic inner wheel (1820) is embedded can drive the optical fiber (1850) moving, and a driven wheel (1840) has its tread contacting with the optical fiber on the opposite side of the drive wheel. If the drive wheel (1820 & 1830) is dialed or rotated by a human finger, the optical fiber moves in either Z or −Z direction accordingly. Besides, a safety switch in-series connecting to the power on/off switch of an external laser source ensures the use of laser with physician's prudence. The safety switch is turned on once the drive wheel (1820 & 1830) is dialed and latched at a position, and it indicates that a distal tip of the optical fiber protrudes out of the distal end of the endoscope and the setup is ready for a laser therapeutic procedure.

The fourth implementation of the optical fiber placement device is shown in FIG. 21 and FIG. 22. An optical fiber holder (20_4) inside the handle (160) holding a section of the optical fiber (11_8) is movable in the Z and −Z direction. A soft rubber outer wheel (20_3) in which a hard plastic inner wheel (20_2) is embedded can drive the optical fiber (11_8) moving, and a driven wheel (20_5) has its tread contacting with the optical fiber on the opposite side of the drive wheel (20_2 & 20_3).

If the drive wheel (20_2 & 20_3) is dialed or rotated by a human finger in direction −Z, the optical fiber will be extended in Z direction accordingly, which is shown in FIG. 21. As shown in FIG. 21, a clockwise rotation of the drive wheel (20_3) drives the optical fiber holder (20_4) to move in the direction Z so that the optical fiber (11_8) carried by the optical fiber holder (20_4) is moved in the direction Z. As the optical fiber holder (20_4) moves in the direction Z with a sufficient distance, it can latch a safety switch (20_6) for turning it on, as a safety feature, so that unlocking an external switch that is in a series connection with the safety switch (20_6) and an external laser generation source.

FIG. 22 illustrates a view of the optical fiber placement device in a non-operational mode. The holder (20_4) is separated from the safety switch (20_6) and moves in −Z direction. The tip of the laser fiber is retracted in direction −Z and the laser generation source is locked at this time.

The above four implementations enable the physician to perform the conventional two-hand endoscopic lithotripsy procedure with only one hand. Moreover, the special design of the safety switch prevents the laser source from being powered on accidentally.

FIG. 23 illustrates a fourth embodiment of the present invention. The endoscope has an optical fiber placement device (2280) entering the endoscope from the 3-way Luer connector (140), and the fiber with ETFE jacket can be placed in the working channel.

FIG. 24 illustrates the distal end, which is wedge-shaped, in detail. A working channel opening (2050), an image sensor (2010), an illumination lens (2020) and an ultra-small pressure sensor (2040) are shown. The ultra-small pressure sensor (2040) is installed at a proper position at the distal end (110).

FIG. 25 illustrates a view of the distal end (110) along the −Z direction. Three openings reserved for image sensor (2010), working channel (2050) and ultra-small pressure sensor (2040) are shown. An external optical placement device is used and the laser fiber reaches the distal end (110) through the working channel (2050).

The lighting source (2020) is selected from µLED/OLED/infrared LED/Laser LED/Laser diode/LED with suitable size(s), shape, intensity, and other desired parameters.

FIG. 26 is a sectional view of the catheter (120) along Z direction at D-D position. The six-wire bundle (F) is for electrically connecting the image sensor and LED lighting source at tip to a small PCB inside the endoscope handle. A pair of steel wires (521 & 522) are placed symmetrically along the working channel (2050). The steel wires (521 & 522) are soldered to the bend portion (170) and the control lever (150) to control deflections of the distal end (110). A conduit for the ultra-small pressure sensor (2040) is placed close to the bundle.

An independent optical fiber placement device (2280) is shown in FIG. 27. The optical fiber placement device (2280) is independent from the handle (160), and the fiber can enter the working channel from 3-way Luer connector (140). The fiber can be pushed towards the distal end (110) by sliding the slider (2281) in direction H.

FIG. 28 illustrates the structure of bend portion (170).

FIG. 29 illustrates the structure of catheter (120). The catheter has three layers. The middle layer of catheter (120) is made of stainless steel weave mesh and the inner-most layer is made of PEBAX. An outer-layer is made of a synthetic material mixing the graphene nano-filler to enhance the thermal conductivity and improve the heat dissipation of the distal end (110).

The invention claimed is:

1. An endoscope or medical tube (EMT) comprising
  a. an endoscope handle, configured and dimensioned to require only one hand of a user (physician, nurse, etc.) for controlling and operating the endoscope handle, comprising mechanical, electronic, electrical, and optical components;
  b. an elongated conduit coupled and controlled with/by the endoscope handle, expressed in an X-Y-Z Cartesian coordinate system with a tubular cross section lying in a X-Y plane and a tubular axis Z perpendicular to the X-Y plane and pointing towards a distal direction of the conduit defined as a Z-direction, comprising:
     i. a distal end configured and dimensioned for insertion into a patient's organ; and
     ii. a proximal end coupled with the endoscope handle, with a sufficient length from the distal end depending on a specific application of the EMT;
  c. at least one optical fiber (OF) partially embedded in and along the conduit and the endoscope handle, partially extended out of the endoscope handle, and configured and dimensioned movable in the Z and −Z directions; and
  d. at least one optical fiber placement device (OFPD) for holding and moving the optical fiber (OF) in the Z or −Z directions, wherein the OFPD comprises an implementation (13_6) built as a detachable optical fiber placement device (DOFPD) (13_6) that can be inserted into a proximal end of the endoscope handle or into a proximal end of the working channel, the DOFPD (13_6) comprises
     i. an optical fiber box (13_6-4) as a fixture built inside the DOFPD;
     ii. an optical fiber holder (13_6-5) inside the optical fiber box (13_6-4) wherein the optical fiber holder (13_6-5) holds a section of the first optical fiber (FOF) or the second optical fiber (SOF) and the optical fiber holder (13_6-5) is movable in the Z and −Z directions;
     iii. an optical fiber slider (13_6-2) comprising
        1. a sliding block (13_6-2) having a rugged surface facing the Y direction, wherein the sliding block is slid-able by a human finger in both Z and −Z directions, positioned outside a housing of endoscope handle but coupled with the optical fiber holder (13_6-5) via a coupler (13_6-3) between the optical fiber slider (13_6-2) and the optical fiber holder (13_6-5); and
        2. a retractable control stick (RCS) (13_6-3), perpendicularly going through the sliding block, movable and latch-able in the Y and −Y directions and latch-able when an outer end of the retractable control stick (RCS) is pressed by a human finger once in the −Y direction, wherein more specifically,
           i. assuming the RCS is at a position as its outer end is at a farthest position from a surface of the optical fiber slider, if the retractable control stick (13_6-3) is pressed by a human finger once in the −Y direction and latched with the outer end of the RCS at a nearest position from the surface of the RCS, the optical fiber will be moved with a small step of about one or a few millimeters in the Z direction; and
           ii. assuming the RCS is at a position as its outer end is at a nearest from the surface of the optical fiber slider if the retractable control stick (13_6-3) is pressed once again in the −Y direction and then released by a human finger, the optical fiber will be moved in a small step of about one or a few millimeters in the −Z direction;
     iv. an optical fiber lock (13_6-1), slid-able in both Z and −Z directions, positioned close to the optical fiber slider (13_6-2) at the housing of the endoscope handle along the Z direction, wherein
        1. if the optical fiber lock (13_6-1) is slid to a position separated from the optical fiber slider (13_6-2), a bendable part of the optical fiber slider (13_6-2) will be pushed wide open against a rugged side wall of an opening (1201) of the DOFPD so that the optical fiber slider (13_6-2) will be locked and un-slid-able; and
        2. if the optical fiber lock (13_6-1) is slid to a position combing and joining the optical fiber slider (13_6-2), the optical fiber slider becomes unlocked and slid-able in either Z direction or −Z direction so that the optical fiber becomes slid-able in either Z direction or −Z direction by following a movement of the optical fiber slider (13_6-2);
     v. one or more pairs of coupled teeth wherein a set of teeth is built on edges of the optical fiber slider (13_6-2) and another set of teeth is built on sidewalls of the opening (1201) of the DOFPD; and
     vi. at least one laser safety switch (LSS), inside the DOFPD, in series connection with an external on/off switch for turning on/off an external laser generation source, wherein the LSS is turned on once the retractable control stick (RCS) (13_6-3) is pressed and latched; Otherwise, the LSS is turned off.

2. The EMT of claim 1 wherein the optical fiber(s) (OF(s)) comprise(s)
  a. a first optical fiber(s) connectable to a lighting source at a proximal tip of the first optical fiber, including a laser generation source for a surgical treatment;
  b. a second optical fiber(s), if needed/desired, connectable to a lighting source at a proximal tip of the second optical fiber, including a laser generation source for a surgical treatment; and
  c. a third optical fiber(s), if needed/desired, comprising a pressure sensor chosen from a group of pressure sensors including an MEMS at a distal tip of the third optical fiber and is connectable, at the proximal tip of the third optical fiber, to a coupled device supporting the MEMS pressure sensor.

3. The EMT of claim 1 wherein the conduit further comprises
  a. a video camera system (VCS), inside the distal end having a first end pointing to the Z direction and a second end pointing to the −Z direction and sized suitable for endoscopy, comprising
  i. one or more image sensors IS(s) facing one or more directions wherein at least a first image sensor (FIS) faces out towards the Z direction; and
  ii. one or more lighting sources (LS(s)), provided by at least one from a group of MicroLED, OLED, infrared LED, Laser LED, Laser diode, and LED;
b. a bend/deflection portion (BP) having a first end connected to the second end of the distal end (DE) (1) and a second end, sized suitable for endoscopy;
c. a catheter (8) having a first end connected to the second end of the bend portion (BP) (6) and a second end, sized suitable for endoscopy or medical tubing.

4. The EMT of claim 3 wherein
a. the VCS (3) comprises
  i. a second image sensor, in addition to the first image sensor (FIS), facing out towards an X direction;
  ii. a third image sensor, in addition to the first image sensor (FIS) and the second image sensor (SIS), facing out towards a Y direction; and
  iii. a fourth image sensor, in addition to the first image sensor (FIS), the second image sensor (SIS), and the third image sensor (TIS), facing out towards a −Y direction;
b. the distal end (DE) (1) comprises a transparent shell (TS) as a housing for hosting the VCS wherein the transparent shell (TS) comprises
  i. a mixture of polymer composite material and a graphene nano-filler for enhancing thermal conductivity; and
  ii. a shape with smooth edges;
c. the LS(s) comprise/s a heat sink (HS) comprising a graphene nano-filler mixed in an adhesive material for enhancing thermal conductivity, wherein the adhesive material is used as an adhesive;
d. the LS(s) is/are located on one or more sides of an image sensor (IS) if viewed from a top for positioning the light source(s) (LS(s));
e. the image sensor(s)' orientation(s) is/are adjustable via the control device (CD); and
f. the bend portion (BP) comprises a bend part made of chained devices tied to the pair of steel wires (SW), and it is fully covered by protective composite materials; the bend portion (BP) can be deflected up to 275 degrees in two directions by the CD,
  i. wherein the chained devices comprise
    1. a metal material having high strength and heat transfer conductivity for dissipating heat out from the distal end (DS);
    2. a carbon fiber material having high strength and heat transfer conductivity for dissipating heat out from the distal end (DS); or
    3. a synthetic material mixed with graphene nano-filler for enhancing its heat transfer conductivity to dissipate heat out from the distal end (DS),
g. the distal end (DS), the bend portion (BP), and the catheter are configured and dimensioned for specific applications of the EMT; and
h. the catheter comprises
  i. an inner-most layer of a medical grade of material;
  ii. a middle layer (ML) comprising a stainless-steel weave mesh (SSWM) wherein (ML) comprises a thermal contact with the HS in the LS(s) and a thermal contact with the transparent shell (TS) in the distal end for dissipating heat out from the LS(s) and the IS(s); and
  iii. an outer-most layer of a medical grade of material.

5. The EMT of claim 4 wherein
a. the inner-most layer comprises a PEBAX material and wherein the outer-most layer comprises a PEBAX material; and
b. the outer-most layer comprises a graphene nano-filler, mixed with a synthetic material, for enhancing heat transfer conductivity to dissipate heat out from the distal end (DS) area.

6. The EMT of claim 4 wherein the middle layer (ML) comprises a carbon fiber weave mesh (CFWM) for enhancing its strength and heat transfer conductivity to dissipate heat out from the distal end (DS) area and for reducing a thickness of the middle layer (ML).

7. The EMT of claim 1 wherein the endoscope handle further comprises a control device (CD), coupled with the second end of the catheter, for controlling the distal end (DE) and accessories for medical procedures.

8. The EMT of claim 7 wherein the CD comprises
a. a strain relief;
b. a left case;
c. a right case;
d. an angulation control lever (ACL) for controlling a position of the distal end (DE) via the SC;
e. a tool inlet port (TIP);
f. an irrigation port (IP);
g. a video signal and control cable;
h. a video signal and control cable connector for communication with an external video processor (EVP); and
i. a circuit for providing power to the IS(s) and the LS(s) for receiving video signals from the IS(s), and for sending video signals to the EVP.

9. The EMT of claim 8 wherein the angulation control lever (ACL) can be operated at various angles for adjusting the distal end (DE) at desired angles accordingly.

10. The EMT of claim 8
a. wherein the strain relief comprises one or more from:
  i. a synthetic material;
  ii. a metal material, including aluminum, for enhancing heat transfer conductivity to dissipate heat out from the distal end (DS) area; and
  iii. a graphene nano-filler, mixed with a synthetic material, for enhancing heat transfer conductivity to dissipate heat out from the distal end (DS) area; and
b. wherein the left case and right case the comprise one or more from:
  i. a synthetic material;
  ii. a metal material, including aluminum, for enhancing heat transfer conductivity to dissipate heat out from the distal end (DS) area; and
  iii. a graphene nano-filler, mixed with a synthetic material, for enhancing heat transfer conductivity to dissipate heat out from the distal end (DS) area.

11. The EMT of claim 1 wherein the conduit further comprises
a. a pair of steel wires (SW) going through the control device (CD) and the catheter (8) for controlling the bend portion (BP); and
b. a working channel (WC) starting from the CD and ending at the distal end (DE) (1) through the catheter and the bend portion (BP) for medical treatment tools or medications accessing needed areas inside a patient's organ from the CD to the distal end (DE), wherein the working channel (WC) comprises an oval shaped cross section for allowing water or fluid to flow in through the working channel (WC) (5) as needed.

12. The EMT of claim 1 wherein the distal end (DE) comprises an outlet port (OP) connected to the WC, connected to the IP via the distal end (DE), the bend portion (BP), the catheter (8), and the control device (CD), for medical treatment tools or medications, fed at the tool inlet port (TIP), accessing needed areas inside a patient's organ, wherein the oval shaped cross-section of the working channel WC allows water or fluid to flow in from the irrigation port (IP) to the outlet port OP at the distal end (DE) via the working channel (WC) while a tooling catheter/tube/wire/cable/string with a round shaped cross-section occupies the working channel (WC).

13. The EMT of claim 12 wherein the outlet port (OP) is formed on the transparent shell (TS) with a slope of 53° angle from an XY plane in the XYZ Cartesian coordination system.

14. The EMT of claim 1 wherein the distal end (DE) further comprises a round shaped cross section, with a minimized perimeter, that houses a square or rectangular shaped image sensor IS and an oval shaped working channel (WC) next to each other in a cross-section view forming two hollow spaces inside distal end (DE), in the round shaped cross section, that are filled with one or more lighting sources (LS(s)) in each hollow space for providing light to the first image sensor (FIS) yet not occupying any extra space so that a perimeter of the distal end (DE) at the round shaped cross-section is minimized.

15. The EMT of claim 1 wherein the OFPD applies a similar mechanism to one of pencil lead's placement and movement in a mechanical pencil.

16. The EMT of claim 1 wherein the OFPD further comprises an implementation (13_6) built as a detachable optical fiber placement device (DOFPD) (13_6) that can be inserted into a proximal end of the endoscope handle or into a proximal end of the working channel, the DOFPD (13_6) comprises
  a. an optical fiber box (13_6-4) as a fixture built inside the DOFPD;
  b. an optical fiber holder (13_6-5) inside the optical fiber box (13_6-4) wherein the optical fiber holder (13_6-5) holds a section of the first optical fiber (FOF) or the second optical fiber (SOF) and the optical fiber holder (13_6-5) is movable in the Z and −Z directions;
  c. an optical fiber slider (13_6-2) comprising
    i. a sliding block (13_6_2) having a rugged surface facing the Y direction, wherein the sliding block is slid-able by a human finger in both Z and −Z directions, positioned outside a housing of the endoscope handle but coupled with the optical fiber holder (13_6-5) via a coupler (13_6-4) between the optical fiber slider (13_6-2) and the optical fiber holder (13_6-5); and
    ii. a retractable control stick (RCS) (13_6-3), perpendicularly going through the sliding block, movable and latch-able in the Y and −Y directions and latch-able when an outer end of the retractable control stick (RCS) is pressed by a human finger once in the −Y direction, wherein more specifically,
      1. assuming the RCS is at a position as its outer end is at a farthest position from a surface of the optical fiber slider, if the retractable control stick (13_6-3) is pressed by a human finger once in the −Y direction and latched with the outer end of the RCS at a nearest position from the surface of the RCS, the optical fiber will be moved with a small step of about one or a few millimeters in the Z direction; and
      2. assuming the RCS is at a position as its outer end is at a nearest from the surface of the optical fiber slider if the retractable control stick (13_6-3) is pressed once again in the −Y direction and then released by a human finger, the optical fiber will be moved in a small step of about one or a few millimeters in the −Z direction;
  d. an optical fiber lock (13_6-1), slid-able in both Z and −Z directions, positioned close to the optical fiber slider (13_6-2) at the housing of the endoscope handle along the Z direction, wherein
    i. if the optical fiber lock (13_6-1) is slid to a position separated from the optical fiber slider (13_6-2), a bendable part of the optical fiber slider (13_6-2) will be pushed wide open against a rugged side wall of an opening (1201) of the DOFPD so that the optical fiber slider (13_6-2) will be locked and un-slid-able; and
    ii. if the optical fiber lock (13_6-1) is slid to a position combing and joining the optical fiber slider (13_6-2), the optical fiber slider becomes unlocked and slid-able in either Z direction or −Z direction so that the optical fiber becomes slid-able in either Z direction or −Z direction by following a movement of the optical fiber slider (13_6-2);
  e. one or more pairs of coupled teeth wherein a set of teeth is built on edges of the optical fiber slider (13_6-2) and another set of teeth is built on sidewalls of the opening (1201) of the DOFPD; and
  f. at least one laser safety switch (LSS), inside the DOFPD, in series connection with an external on/off switch for turning on/off an external laser generation source, wherein the LSS is turned on once the retractable control stick (RCS) (13_6-3) is pressed and latched; Otherwise, the LSS is turned off.

17. The EMT of claim 1 wherein the OFPD further comprises, an implementation built either inside the endoscope handle or as a detachable optical fiber placement device (DOFPD) (17_6) to be inserted into a proximal end of the endoscope handle or into a proximal end of the working channel, the DOFPD (17_6) comprises
  a. a drive wheel comprising an inner wheel (1820) and outer wheel (1830), wherein the drive wheel's tread has a gentle contact with the optical fiber (OF);
  b. a driven wheel (1840), wherein the driven wheel's tread has a gentle contact with the optical fiber on the opposite side; while the drive wheel is dialed or rotated by a human finger, the optical fiber will move in either Z or −Z direction accordingly;
  c. at least one laser safety switch (LSS), inside the DOFPD, in series connection with an external on/off switch for turning on/off an external laser generation source, wherein the LSS is turned on once the drive wheel is dialed and latched at a position indicating that a distal tip of the optical fiber protrudes out of the distal end of the endoscope and the setup is ready for a laser therapeutic procedure; Otherwise, the LSS is turned off; and
  d. marks on either the drive wheel or the driven wheel for indicating positions of the distal tip of the OF.

18. The EMT of claim 1 wherein the OFPD further comprises, an implementation built either inside the endoscope handle or as a detachable optical fiber placement device (DOFPD) (20_0) to be inserted into a proximal end of the endoscope handle or into a proximal end of the working channel, the DOFPD (20-0) comprises a. a drive wheel comprising an inner wheel (20_2) and outer wheel (20_3), wherein the drive wheel's tread has a contact with a special optical fiber holder (SOFH) (20_4) that holds the optical fiber (OF) (11_8);

b. a driven wheel (20_5), wherein the driven wheel's tread has a contact with the special optical fiber holder (SOFH) on the opposite side; while the drive wheel is dialed or rotated by a human finger, the optical fiber moves in either Z or −Z direction accordingly;

c. at least one laser safety switch (LSS) (20_6), inside the DOFPD, in series connection with an external on/off switch for turning on/off an external laser generation source, wherein the LSS is turned on once the drive wheel is dialed and latched at a position indicating that a distal tip of the OF protrudes out of the distal end of the endoscope and the setup is ready for a laser therapeutic procedure; Otherwise, the LSS is turned off; and d. marks on either the drive wheel or the driven wheel for indicating positions of the distal tip of the OF.

19. The EMT of claim 1 wherein the EMT is intended for a single use and the endoscope handle is intended for being operated by only one hand of the user.

20. An endoscope or medical tube (EMT) comprising a. an endoscope handle, configured and dimensioned to require only one hand of a user (physician, nurse, etc.) for controlling and operating the endoscope handle, comprising mechanical, electronic, electrical, and optical components;

b. an elongated conduit coupled and controlled with/by the endoscope handle, expressed in an X-Y-Z Cartesian coordinate system with a tubular cross section lying in a X-Y plane and a tubular axis Z perpendicular to the X-Y plane and pointing towards a distal direction of the conduit defined as a Z-direction, comprising:
  i. a distal end configured and dimensioned for insertion into a patient's organ; and
  ii. a proximal end coupled with the endoscope handle, with a sufficient length from the distal end depending on a specific application of the EMT;

c. at least one optical fiber (OF) partially embedded in and along the conduit and the endoscope handle, partially extended out of the endoscope handle, and configured and dimensioned movable in the Z and −Z directions; and d. at least one optical fiber placement device (OFPD) for holding and moving the optical fiber (OF) in the Z or −Z directions, wherein the OFPD comprises an implementation partially built inside the endoscope handle, the implementation comprises
  a. an optical fiber box (11_6) as a fixture built inside the endoscope handle;
  b. an optical fiber holder (13_6-5) inside the optical fiber box (11_6) wherein the optical fiber holder (13_6-5) holds a section of the optical fiber (OF) and the optical fiber holder (13_6-5) is movable in the Z and −Z directions;
  c. an optical fiber slider (13_6-2) comprising
    i. a sliding block (13_6_2) having a rugged surface facing the Y direction, wherein the sliding block is slid-able by a human finger in both Z and −Z directions, positioned outside a housing of the endoscope handle but coupled with the optical fiber holder (13_6-5) via a coupler (13_6-4) between the optical fiber slider (13_6-2) and the optical fiber holder (13_6-5); and
    ii. a retractable control stick (RCS). (13_6-3), perpendicularly going through the sliding block, movable and latch-able in the Y and −Y directions and latch-able when the retractable control stick (RCS) is pressed by a human finger once in the −Y direction, wherein more specifically,
      1. assuming the RCS is at a position as its outer end is at a farthest position from a surface of the optical fiber slider, if the retractable control stick (13_6-3) is pressed by a human finger once in the −Y direction and latched with the outer end of the RCS at a nearest position from the surface of the RCS, the optical fiber will be moved with a small step of about one or a few millimeters in the Z; and
      2. assuming the RCS is at a position as its outer end is at a nearest position from the surface of the optical fiber slider if the retractable control stick (13_6-3) is pressed once again in the −Y direction and then released by a human finger, the optical fiber will be moved in a small step of about one or a few millimeters in the −Z direction;
  d. an optical fiber lock (13_6-1), slid-able in both Z and −Z directions, positioned close to the optical fiber slider (13_6-2) at the housing of the endoscope handle along the Z direction, wherein
    i. if the optical fiber lock (13_6-1) is slid to a position separated from the optical fiber slider (13_6-2), a bendable part of the optical fiber slider (13_6-2) will be pushed wide open against a rugged side wall of an opening (1201) of the endoscope handle so that the optical fiber slider (13_6-2) will be locked and un-slid-able; and
    ii. if the optical fiber lock (13_6-1) is slid to a position combing and joining the optical fiber slider (13_6-2), the optical fiber slider becomes unlocked and slid-able in either Z direction or −Z direction so that the optical fiber becomes slid-able in either Z direction or −Z direction by following a movement of the optical fiber slider (13_6-2);
  e. one or more pairs of coupled teeth wherein a set of teeth is built on edges of the optical fiber slider (13_6-2) and another set of teeth is built on sidewalls of the opening (1201) of the endoscope handle; and
  f. at least one laser safety switch (LSS), inside the endoscope handle, in series connection with an external laser on/off switch for turning on/off an external laser generation source, wherein the LSS is turned on once the retractable control stick (RCS) (13_6-3) is pressed and latched otherwise the LSS is turned off.

21. The EMT of claim 20 wherein the optical fther(s) (OF(s)) comprise(s)

a. a first optical fiber(s) connectable to a lighting source at a proximal tip of the first optical fiber, including a laser generation source for a surgical treatment;

b. a second optical fiber(s), if needed/desired, connectable to a lighting source at a proximal tip of the second optical fiber, including a laser generation source for a surgical treatment; and c. a third optical fiber(s), if needed/desired, comprising a pressure sensor chosen from a group of pressure sensors including an MEMS at a distal tip of the third optical fiber and is connectable, at the proximal tip of the third optical fiber, to a coupled device supporting the MEMS pressure sensor.

22. The EMT of claim 20 wherein the conduit further comprises
  d. a video camera system (VCS), inside the distal end having a first end pointing to the Z direction and a second end pointing to the −Z direction and sized suitable for endoscopy, comprising
    iii. one or more image sensors IS(s) facing one or more directions wherein at least a first image sensor (FIS) faces out towards the Z direction; and
    iv. one or more lighting sources (LS(s)), provided by at least one from a group of MicroLED, OLED, infrared LED, Laser LED, Laser diode, and LED;
  e. a bend/deflection portion (BP) having a first end connected to the second end of the distal end (DE) (1) and a second end, sized suitable for endoscopy;
  f. a catheter (8) having a first end connected to the second end of the bend portion (BP) (6) and a second end, sized suitable for endoscopy or medical tubing.

23. The EMT of claim 22 wherein
  a. the VCS (3) comprises
    i. a second image sensor, in addition to the first image sensor (FIS), facing out towards an X direction;
    ii. a third image sensor, in addition to the first image sensor (FIS) and the second image sensor (SIS), facing out towards a Y direction; and
    iii. a fourth image sensor, in addition to the first image sensor (FIS), the second image sensor (SIS), and the third image sensor (TIS), facing out towards a −Y direction;
  b. the distal end (DE) (1) comprises a transparent shell (TS) as a housing for hosting the VCS wherein the transparent shell (TS) comprises
    i. a mixture of polymer composite material and a graphene nano-filler for enhancing thermal conductivity; and
    ii. a shape with smooth edges;
  c. the LS(s) comprise/s a heat sink (HS) comprising a graphene nano-filler mixed in an adhesive material for enhancing thermal conductivity, wherein the adhesive material is used as an adhesive;
  d. the LS(s) is/are located on one or more sides of an image sensor (IS) if viewed from a top for positioning the light source(s) (LS(s));
  e. the image sensor(s)' orientation(s) is/are adjustable via the control device (CD); and
  f. the bend portion (BP) comprises a bend part made of chained devices tied to the pair of steel wires (SW), and it is fully covered by protective composite materials; the bend portion (BP) can be deflected up to 275 degrees in two directions by the CD,
    i. wherein the chained devices comprise
      1. a metal material having high strength and heat transfer conductivity for dissipating heat out from the distal end (DS);
      2. a carbon fiber material having high strength and heat transfer conductivity for dissipating heat out from the distal end (DS); and/or
      3. a synthetic material mixed with graphene nano-filler for enhancing its heat transfer conductivity to dissipate heat out from the distal end (DS).
  g. the distal end (DS), the bend portion (BP), and the catheter are configured and dimensioned for specific applications of the EMT; and
  h. the catheter comprises
    i. an inner-most layer of a medical grade of material;
    ii. a middle layer (ML) comprising a stainless-steel weave mesh (SSWM) wherein (ML) comprises a thermal contact with the HS in the LS(s) and a thermal contact with the transparent shell (TS) in the distal end for dissipating heat out from the LS(s) and the IS(s); and
    iii. an outer-most layer of a medical grade of material.

24. The EMT of claim 23 wherein
  a. the inner-most layer comprises a PEBAX material and wherein the outer-most layer comprises a PEBAX material; and
  b. the outer-most layer comprises a graphene nano-filler, mixed with a synthetic material, for enhancing heat transfer conductivity to dissipate heat out from the distal end (DS) area.

25. The EMT of claim 23 wherein the middle layer (ML) comprises a carbon fiber weave mesh (CFWM) for enhancing its strength and heat transfer conductivity to dissipate heat out from the distal end (DS) area and for reducing a thickness of the middle layer (ML).

26. The EMT of claim 20 wherein the endoscope handle further comprises a control device (CD), coupled with the second end of the catheter, for controlling the distal end (DE) and accessories for medical procedures.

27. The EMT of claim 26 wherein the CD comprises
  a. a strain relief;
  b. a left case;
  c. a right case;
  d. an angulation control lever (ACL) for controlling a position of the distal end (DE) via the SC;
  e. a tool inlet port (TIP);
  f. an irrigation port (IP);
  g. a video signal and control cable;
  h. a video signal and control cable connector for communication with an external video processor (EVP); and
  i. a circuit for providing power to the IS(s) and the LS(s) for receiving video signals from the IS(s), and for sending video signals to the EVP.

28. The EMT of claim 27 wherein the angnla don control lever (ACL) can be operated at various angles for adjusting the distal end (DE) at desired angles accordingly.

29. The EMT of claim 27
  a. wherein the strain relief Comprises one or more from::
    i. a synthetic material;
    ii. a metal material, including aluminum, for enhancing heat transfer conductivity to dissipate heat out from the distal end (DS) area; and
    iii. a graphene nano-filler, mixed with a synthetic material, for enhancing heat transfer conductivity to dissipate heat out from the distal end (DS) area; and
  b. wherein the left case and right case the comprise one or more from:
    i. a synthetic material;
    ii. a metal material, including aluminum, for enhancing heat transfer conductivity to dissipate heat out from the distal end (DS) area; and
    iii. a graphene nano-filler, mixed with a synthetic material, for enhancing heat transfer conductivity to dissipate heat out from the distal end (DS) area.

30. The EMT of claim 20 wherein the conduit further comprises
  a. a pair of steel wires (SW) going through the control device (CD) and the catheter (8) for controlling the bend portion (BP); and
  b. a working channel (WC) starting from the CD and ending at the distal end (DE) (1) through the catheter and the bend portion (BP) for medical treatment tools or medications accessing needed areas inside a patient's organ from the CD to the distal end (DE), wherein, the working channel (WC) comprises an oval shaped cross section for allowing water or fluid to flow in through the working channel (WC) (5) as needed.

31. The EMT of claim 20 wherein the distal end (DE) comprises an outlet port (OP) connected to the WC, connected to the IP via the distal end (DE), the bend portion (BP), the catheter (8), and the control device (CD), for medical treatment tools or medications, fed at the tool inlet port (TIP), accessing needed areas inside a patient's organ, wherein the oval shaped cross-section of the working channel WC allows water or fluid to flow in from the irrigation port (IP) to the outlet port OP at the distal end (DE) via the working channel (WC) while a tooling catheter/tube/wire/cable/string with a round shaped cross-section occupies the working channel (WC).

32. The EMT of claim 31 wherein the outlet port (OP) is formed on the transparent shell (TS) with a slope of 53° angle from an XY plane in the XYZ Cartesian coordination system.

33. The EMT of claim 20 wherein the distal end (DE) further comprises a round shaped cross section, with a minimized perimeter, that houses a square or rectangular shaped image sensor IS and an oval shaped working channel (WC) next to each other in a cross-section view forming two hollow spaces inside distal end (DE), in the round shaped cross section, that are filled with one or more lighting sources (LS(s)) in each hollow space for providing light to the first image sensor (FIS) yet not occupying any extra space so that a perimeter of the distal end (DE) at the round shaped cross-section is minimized.

34. The EMT of claim 20 wherein the OFPD applies a similar mechanism to one of pencil lead's placement and movement in a mechanical pencil.

35. The EMT of claim 20 wherein the OFPD further comprises an implementation (13_6) built as a detachable optical fiber placement device (DOFPD) (13_6) that can be inserted into a proximal end of the endoscope handle or into a proximal end of the working channel, the DOFPD (13_6) comprises a. an optical fiber box (13_6-4) as a fixture built inside the DOFPD;
b. an optical fiber holder (13_6-5) inside the optical fiber box (13_6-4) wherein the optical fiber holder (13_6-5) holds a section of the first optical fiber (FOF) or the second optical fiber (SOF) and the optical fiber holder (13_6-5) is movable in the Z and −Z directions;
c. an optical fiber slider (13_6-2) comprising
  i. a sliding block (13_6-2) having a rugged surface facing the Y direction, wherein the sliding block is slid-able by a human finger in both Z and −Z directions, positioned outside a housing of endoscope handle but coupled with the optical fiber holder (13_6-5) via a coupler (13_6-3) between the optical fiber slider (13_6-2) and the optical fiber holder (13_6-5); and
  ii. a retractable control stick (RCS) (13_6-3), perpendicularly going through the sliding block, movable and latch-able in the Y and −Y directions and latch-able when an outer end of the retractable control stick (RCS) is pressed by a human finger once in the −Y direction, wherein more specific ally,
    1. assuming the RCS is at a position as its outer end is at a farthest position from a surface of the optical fiber slider, if the retractable control stick (13_6-3) is pressed by a human finger once in the −Y direction and latched with the outer end of the RCS at a nearest position from the surface of the RCS, the optical fiber will be moved with a small step of about one or a few millimeters in the Z direction; and
    2. assuming the RCS is at a position as its outer end is at a nearest from the surface of the optical fiber slider if the retractable control stick (13_6-3) is pressed once again in the −Y direction and then released by a human finger, the optical fiber will be moved in a small step of about one or a few millimeters in the −Z direction;
d. an optical fiber lock (13_6-1), slid-able in both Z and −Z directions, positioned close to the optical fiber slider (13_6-2) at the housing of the endoscope handle along the Z direction, wherein
  i. if the optical fiber lock (13_6-1) is slid to a position separated from the optical fiber slider (13_6-2), a bendable part of the optical fiber slider (13_6-2) will be pushed wide open against a rugged side wall of an opening (1201) of the DOFPD so that the optical fiber slider (13_6-2) will be locked and un-slid-able; and
  ii. if the optical fiber lock (13_6-1) is slid to a position combing and joining the optical fiber slider (13_6-2), the optical fiber slider becomes unlocked and slid-able in either Z direction or −Z direction so that the optical fiber becomes slid-able in either Z direction or −Z direction by following a movement of the optical fiber slider (13_6-2);
e. one or more pairs of coupled teeth wherein a set of teeth is built on edges of the optical fiber slider (13_6-2) and another set of teeth is built on sidewalls of the opening (1201) of the DOFPD; and
f. at least one laser safety switch (LSS), inside the DOFPD, in series connection with an external on/off switch for turning on/off an external laser generation source, wherein the LSS is turned on once the retractable control stick (RCS) (13_6-3) is pressed and latched; Otherwise, the LSS is turned off.

36. The EMT of claim 20 wherein the OFPD further comprises an implementation built either inside the endoscope handle or as a detachable optical fiber placement device (DOFPD) (17_6) to be inserted into a proximal end of the endoscope handle or into a proximal end of the working channel, the DOFPD (17_6) comprises a. a drive wheel comprising an inner wheel (1820) and outer wheel (1830), wherein the drive wheel's tread has a gentle contact with the optical fiber (OF);
b. a driven wheel (1840), wherein the driven wheel's tread has a gentle contact with the optical fiber on the opposite side; while the drive wheel is dialed or rotated by a human finger, the optical fiber will move in either Z or −Z direction accordingly;
c. at least one laser safety switch (LSS), inside the DOFPD, in series connection with an external on/off switch for turning on/off an external laser generation source, wherein the LSS is turned on once the drive wheel is dialed and latched at a position indicating that a distal tip of the optical fiber protrudes out of the distal end of the endoscope and the setup is ready for a laser therapeutic procedure; Otherwise, the LSS is turned off; and
d. marks on either the drive wheel or the driven wheel for indicating positions of the distal tip of the OF.

37. The EMT of claim 20 wherein the OFPD further comprises an implementation built either inside the endoscope handle or as a detachable optical fiber placement device (DOFPD) (20_0) to be inserted into a proximal end of the endoscope handle or into a proximal end of the working channel, the DOFPD (20_0) comprises
- a. a drive wheel comprising an inner wheel (20_2) and outer wheel (20_3), wherein the drive wheel's tread has a contact with a special optical fiber holder (SOFH) (20_4) that holds the optical fiber (OF) (11_8);
- b. a driven wheel (205), wherein the driven wheel's tread has a contact with the special optical fiber holder (SOFH) on the opposite side; while the drive wheel is dialed or rotated by a human finger, the optical fiber moves in either Z or $_7$Z direction accordingly;
- c. at least one laser safety switch (LSS) (20_6), inside the DOFPD, in series connection with an external on/off switch for turning on/off an external laser generation source, wherein the LSS is turned on once the drive wheel is dialed and latched at a position indicating that a distal tip of the OF protrudes out of the distal end of the endoscope and the setup is ready for a laser therapeutic procedure; Otherwise, the LSS is turned off; and
- d. marks on either the drive wheel or the driven wheel for indicating positions of the distal tip of the OF.

38. The EMT of claim 20 wherein the EMT is intended for a single use and the endoscope handle is intended for being operated by only one hand of the user.

* * * * *